(12) United States Patent
Pinsky et al.

(10) Patent No.: US 6,972,175 B2
(45) Date of Patent: Dec. 6, 2005

(54) INHIBITION OF EGR-1 EXPRESSION BY PPAR-GAMMA AGONISTS AND RELATED COMPOSITIONS AND METHODS

(76) Inventors: David Pinsky, 33 Barton North Dr., Ann Harbor, MI (US) 48105; Tucker Collins, 120 Jerusalem Rd., Cohasset, MA (US) 02025

( * ) Notice: Subject to any disclaimer, the term of this patent is extended or adjusted under 35 U.S.C. 154(b) by 8 days.

(21) Appl. No.: 10/305,504

(22) Filed: Nov. 27, 2002

(65) Prior Publication Data

US 2004/0101902 A1    May 27, 2004

(51) Int. Cl.$^7$ ............................ C12Q 1/68; C12Q 1/02
(52) U.S. Cl. ............................................ 435/6; 435/29
(58) Field of Search ....................................... 435/70.5

(56) References Cited

U.S. PATENT DOCUMENTS 6,486,142 B2    11/2002    Leblance et al.

OTHER PUBLICATIONS

Adams, D.H., and Lloyd, A.R. (1997) Chemokines: leucocyte recruitment and activation cytokines. Lancet 349:490-495 (Exhibit 1).
Brun, R.P., Tontonoz, P., Forman, B.M., Ellis, R., Chen, J., Evans, R.M., and Spiegelman, B.M. (1996) Differential activation of adipogenesis by multiple PPAR isoforms. Genes. Dev. 10:974-984 (Exhibit 2).
Forman, B.M., Tontonoz, P., Chen, J., Brun, R.P., Spiegelman, B.M., and Evans, R.M. (1995) 15-Deoxy-delta 12, 14-prostaglandin J2 is a ligand for the adipocyte determination factor PPAR gamma. Cell 83:803-812 (Exhibit 3).
Furie, M.B., and Randolph, G.J. (1995) Chemokines and tissue injury, Am. J. Pathol. 146:1287-1301 (Exhibit 4).
Gashler, A., and Sukhatme, V. P. (1995) Early growth response protein 1 (Egr-1): prototype of a zinc-finger family of transcription factors. Prog. Nucleic. Acid. Res. Mol. Biol. 50:191-224 (Exhibit 5).
Goldblum, S.E., Wu, K.M., and Jay, M. (1985) Lung myeloperoxidase as a measure of pulmonary leukostasis in rabbits. J. Appl. Physiol. 59:1978-1985 (Exhibit 6).
Heemann, U., Szabo, A., Hamar, P., Muller, V., Witzke, O., Lutz, J., and Philipp, T. (2000) Lipopolysaccharide pretreatment protects from renal ischemia/reperfusion injury: possible connection to an interleukin-6-dependent pathway. Am. J. Pathol. 156:287-293 (Exhibit 7).
Herskowitz, A., Choi, S., Ansari, A.A., and Wesselingh, S. (1995) Cytokine mRNA expression in postischemic/reperfused myocardium. Am. J. Pathol. 146:419-428 (Exhibit 8).
Jiang, C., Ting, A.T., and Seed, B. (1998) PPAR-gamma agonists inhibit production of monocyte inflammatory cytokines. Nature 391:82-6 (Exhibit 9).
Lehmann, J.M., Moore, L.B., Smith-Oliver, T.A., Wilkison, W.O., Willson, T.M., and Kliewer, S.A. (1995) An antidiabetic thiazolidinedione is a high affinity ligand for peroxisome proliferator-activated receptor gamma (PPAR gamma). J. Biol. Chem. 270:12953-12956 (Exhibit 10).
Miura, M., Fu, X., Zhang, Q.W., Remick, D.G., and Fairchild, R.L. (2001) Neutralization of Gro alpha and macrophage inflammatory protein-2 attenuates renal ischemia/reperfusion injury. Am. J. Pathol. 159:2137-2145 (Exhibit 11).
Nakajima, A., Wada, K., Miki, H., Kubota, N., Nakajima, N., Terauchi, Y., Ohnishi, S., Saubermann, L.J., Kadowaki, T., Blumberg, R.S., Nagai, R., and Matsuhashi, N. (2001) Endogenous PPAR gamma mediates anti-inflammatory activity in murine ischemia-reperfusion injury. Gastroenterology 120:460-469 (Exhibit 12).
Nguyen, H.Q., Hoffman-Liebermann, B., and Liebermann, D.A. (1993) The zinc finger transcription factor Egr-1 is essential for and restricts differentiation along the macrophage lineage. Cell 72:197-209 (Exhibit 13).
Okada, M., Fujita, T., Sakaguchi, T., Olson, K.E., Collins, T., Stern, D.M., Yan, S.F., and Pinsky, D.J. (2001) Extinguishing Egr-1-dependent inflammatory and thrombotic cascades after lung transplantation. FASEB. J. 15:2757-2759 (Exhibit 14).
Ricote, M.F., Li, A.C., Willson, T.M., Kelly, C.J., and Glass, C.K. (1998) The peroxisome proliferator-activated receptor-gamma is a negative regulator of macrophage activation. Nature 391:79-82 (Exhibit 15).
Ricote, M., Huang, J.T., Welch, J.S., and Glass, C.K. (1999) The peroxisome proliferator-activated receptor (PPAR-gamma) as a regulator of monocyte/macrophage function. J. Leukoc. Biol. 66:733-739 (Exhibit 16).
Schoonjans, K., Martin, G., Staels, B., Auwerx, J. (1997) Peroxisome proliferator-activated receptors, orphans with ligands and functions. Curr. Opin. Lipidol. 8:159-166 (Exhibit 17).
Venditti, P., Masullo, P., Di Meo, S., and Agnisola, C. (1999) Protection against ischemia-reperfusion induced oxidative stress by vitamin E treatment. Arch. Physiol. Biochem. 107:27-34 (Exhibit 18).
Venditti, P., Masullo, P., Agnisola, C., and Di Meo, S. (2000) Effect of vitamin E on the response to ischemia-reperfusion of Langendorff heart preparations from hyperthyroid rats. Life Sci. 66:697-708 (Exhibit 19).

(Continued)

*Primary Examiner*—Nancy Vogel
(74) *Attorney, Agent, or Firm*—John P. White, Esq.; Cooper & Dunham LLP

(57) ABSTRACT

This invention provides methods for determining whether an agent increases PPAR-γ-mediated inhibition of Egr-1 expression. This invention also provides methods for inhibiting the onset of atherosclerosis in a transplanted organ. This invention further provides numerous methods for treating disorders, and/or inhibiting the onset of disorders or disorder-related complications by using PPAR-γ agonists. This invention still further provides related methods for inhibiting cancer metastasis, treating and inhibiting the onset of a heart attack, and treating burn and crush injuries. Finally, this invention provides related articles of manufacture.

9 Claims, 14 Drawing Sheets

OTHER PUBLICATIONS

Yan, S.F., Tritto, I., Pinsky, D., Liao, H., Huang, J., Fuller, G.F., Brett, J., May, L., and Stern, D. (1995) Induction of interleukin 6 (IL-6) by hypoxia in vascular cells. Central role of the binding site for nuclear factor-IL-6. J. Biol. Chem. 270:11463-11471 (Exhibit 20).

Yan, S.F., Lu, J., Zou, Y.S., Soh-Won, J., Cohen, D. M., Buttrick, P.M., Cooper, D.R., Steinberg, S.F., Mackman, N., Pinsky, D.J., and Stern, D.M. (1999) Hypoxia-associated induction of early growth response-1 gene expression. J. Biol. Chem. 274:15030-15040 (Exhibit 21).

Yan, S.F., Fujita, T., Lu, J., Okada, K., Shan Zou, Y., Mackman, N., Pinsky, D.J., and Stern, D.M. (2000) Egr-1, a master switch coordinating upregulation of divergent gene families underlying ischemic stress. Nature Medicine 6: 1355-1361 (Exhibit 22).

Jiang, Chengyu et al., "PPAR-γ agonists inhibit production of monocyte inflammatory cytokines", Nature, vol. 391, (1998), pp. 82-86.

Nguyen, Hung Q, et al., "The Zinc Finger Transcription Factor Egr-1 Is Essential for and Restricts Differentiation along the Macrophage Lineage", Cell, vol. 72, (1993), pp. 197-209.

Ricote, Mercedes, et al., "The peroxisome proliferators-activated receptorγ (PPARγ) as a regulator of monocyte/macrophage function", Journal of Leukocyte Biology, vol. 66, (1999), pp. 733-739.

Schoonjans, Kristina, et al., "Peroxisome proliferators-activated receptors, orphans with ligands and fuctions", Current Opinion in Lipidology vol. 8, (1997), pp. 159-166.

Mar. 4, 2005 Written Opinion Of The International Searching Authority in connection with International Application No. PCT/US03/37823.

Mar. 4, 2005 International Search Report in connection with PCT/US03/37823.

INHIBITION OF EGR-1 EXPRESSION BY PPAR-GAMMA AGONISTS AND RELATED COMPOSITIONS AND METHODS

This invention was made with funding from the United States Public Health Grants Nos. HL559397 and HL60900. Accordingly, the United States Government has certain rights in this invention.

Throughout this application, various publications are referenced. Full bibliographic citations for these publications are found at the end of the specification immediately preceding the claims. The disclosures of these publications in their entirety are hereby incorporated by reference into this application.

BACKGROUND OF THE INVENTION

Interruption of blood flow to a vital organ sets in motion molecular processes which prime the vasculature for amplification of the inflammatory response, which can rapidly lead to tissue injury upon reestablishment of flow. Although there are a number of components to the ischemic vascular milieu which could affect the subsequent reperfusion response, including reduced oxygen tension, stasis, other substrate deprivation, waste product accumulation, or pH, the response to oxygen deprivation appears to be one of the most highly conserved and potent of these stimuli.

Cells respond to oxygen deprivation by activating programs of gene transcription that are likely to be adaptive in certain circumstances, but which may catalyze significant tissue injury in other circumstances. Programs of gene transcription as part of the cellular response to oxygen deprivation are driven largely by induction/activation and nuclear accumulation of two primary transcription factors, hypoxia-inducible factor-1 (HIF-1), and early growth response gene-1 (Egr-1) (Yan, 2000; Milbrandt, 1987; Gashler, 1995; and Nguyen, 1993). Hypoxia or tissue ischemia triggers rapid induction of Egr-1 mRNA, protein, and nuclear binding activity in a HIF-1-independent manner (Yan, 1999). More recently, it has been demonstrated that the induction of Egr-1 under conditions of ischemic vascular stress is a vital common denominator underlying induction of many different genes which encode diverse activators of inflammation and coagulation. Egr-1 induction therefore sets the stage for subsequent tissue injury during reperfusion (Yan, 2000; and Okada, 2001).

The peroxisome proliferator-activated receptor (PPAR-$\gamma$) is a potentially important transcription factor which modulates the inflammatory response of monocytes, which may underlie some of the anti-inflammatory effects of salicylates in rheumatoid arthritis (Jiang, 1998). PPAR-$\gamma$ ligands were shown to inhibit the production of nitric oxide and macrophage-derived cytokines (i.e., tumor necrosis factor, interleukin (IL-1, and IL-6) at least in part by antagonizing the activation of transcription factors such as nuclear factor-kappaB (NF-$\kappa$B) (Jiang, 1998; and Ricote, 1998). PPAR-$\gamma$, a member of the nuclear hormone receptor superfamily, was originally reported to be highly expressed in adipocytes and to play a critical role in their differentiation (Brun, 1996; and Tontonoz, 1994). It is activated by the natural ligand 15-deoxy-$\Delta^{12,14}$-prostaglandinJ$_2$ (15d-PGJ$_2$) (Forman, 1995) as well as the synthetic ligand thiazolidinedione (Lehmann, 1995).

The PPAR-$\gamma$ gene is expressed in mononuclear phagocytes (Jiang, 1998) and these cells have been shown to respond to hypoxia or ischemia with an exuberant Egr-1-dependent inflammatory response (Yan, 1999; and Yan, 2000).

SUMMARY OF THE INVENTION

This invention provides a method for determining whether an agent increases PPAR-$\gamma$-mediated inhibition of Egr-1 expression comprising (a) (i) contacting the agent with a cell-free system which comprises PPAR-$\gamma$, permits the expression of Egr-1 and permits the inhibition of such expression in the presence of a PPAR-$\gamma$ agonist, and (ii) subjecting the cell-free system to a stimulus known to increase Egr-1 expression in a cell, wherein steps (i) and (ii) are performed concurrently or in sequence;

(b) determining the amount of Egr-1 expression in the cell-free system;

(c) comparing the amount of Egr-1 expression determined in step (b) to the amount of Egr-1 expression observed in the absence of the agent, wherein the amount of Egr-1 expression in the absence of the agent being greater than that in the presence of the agent indicates that the agent inhibits Egr-1 expression; and (d) comparing the amount of Egr-1 expression determined in step (b) with the amount of Egr-1 expression observed in the presence of the agent under conditions known to inhibit PPAR-$\gamma$ activation, wherein the amount of Egr-1 expression in the presence of the agent under such conditions being greater than that determined in step (b) indicates that the agent increases PPAR-$\gamma$-mediated inhibition of Egr-1 expression.

This invention also provides a method for determining whether an agent increases PPAR-$\gamma$-mediated inhibition of Egr-1 expression in a cell comprising (a) (i) contacting the agent with the cell, and (ii) subjecting the cell to a stimulus known to increase Egr-1 expression in a cell, wherein steps (i) and (ii) are performed concurrently or in sequence;

(b) determining the amount of Egr-1 expression in the cell;

(c) comparing the amount of Egr-1 expression determined in step (b) to the amount of Egr-1 expression observed in the cell in the absence of the agent, wherein the amount of Egr-1 expression in the absence of the agent being greater than that in the presence of the agent indicates that the agent inhibits Egr-1 expression in the cell; and (d) comparing the amount of Egr-1 expression determined in step (b) with the amount of Egr-1 expression observed in the presence of the agent and under conditions known to inhibit PPAR-$\gamma$ activation, wherein the amount of Egr-1 expression in the presence of the agent under such conditions being greater than that determined in step (b) indicates that the agent increases PPAR-$\gamma$-mediated inhibition of Egr-1 expression.

This invention further provides a method for determining whether an agent increases PPAR-$\gamma$-mediated inhibition of Egr-1 expression in a subject's cells comprising (a) (i) administering the agent to a non-human subject, and (ii) subjecting the subject to a stimulus known to increase Egr-1 expression in the subject's cells, wherein steps (i) and (ii) are performed concurrently or in sequence;

(b) determining the amount of Egr-1 expression in the subject's cells;

(c) comparing the amount of Egr-1 expression determined in step (b) to the amount of Egr-1 expression observed in the subject's cells in the absence of the agent, wherein the amount of Egr-1 expression in the absence of the agent being greater than that in the presence of the agent indicates that the agent inhibits Egr-1 expression in the subject's cells; and (d) comparing the amount of Egr-1 expression determined in step (b) with the amount of Egr-1 expression observed in the presence of the agent under conditions known to inhibit PPAR-γ activation, wherein the amount of Egr-1 expression in the presence of the agent under such conditions being greater than that determined in step (b) indicates that the agent increases PPAR-γ-mediated inhibition of Egr-1 expression.

This invention further provides a method for inhibiting the onset of atherosclerosis in a transplanted organ comprising administering to the organ recipient a prophylactically effective amount of a PPAR-γ agonist, thereby inhibiting the onset of atherosclerosis in the transplanted organ.

This invention further provides a method for inhibiting the onset of atherosclerosis in a transplanted organ comprising administering to the organ donor, prior to transplantation of the organ to a recipient, a prophylactically effective amount of a PPAR-γ agonist, thereby inhibiting the onset of atherosclerosis in the transplanted organ.

This invention provides numerous methods for treating disorders, and/or inhibiting the onset of disorders or disorder-related complications. The disorders or complications treated, or whose onset is inhibited, include an inflammatory disorder, ischemia, an ischemia/reperfusion-related complication, a multiple organ system dysfunction-related complication, acute respiratory distress syndrome, a central nervous system disorder, a multiple sclerosis-related complication, Alzheimer's disease, a stroke, vascular disease, atherosclerosis, sepsis, a heart attack, a sepsis-related complication, a complication resulting from a procedure wherein a subject's body fluid comes into contact with a foreign surface, a complication resulting from the administration of an extracorporeal oxygenation procedure, and a complication resulting from cardio-pulmonary bypass surgery.

This invention also provides a method for inhibiting the metastasis of a cancerous cell, comprising contacting the cell with an amount of a PPAR-γ agonist effective to inhibit metastasis of the cancerous cell.

This invention further provides a method for treating a subject afflicted with cancer, comprising administering to the subject a therapeutically effective amount of a PPAR-γ agonist, thereby treating the subject.

This invention further provides a method for treating a subject afflicted with a burn injury, comprising administering to the subject a therapeutically effective amount of a PPAR-γ agonist, thereby treating the subject.

This invention further provides a method for treating a subject afflicted with a crush injury, comprising administering to the subject a therapeutically effective amount of a PPAR-γ agonist, thereby treating the subject.

Finally, this invention provides articles of manufacture comprising a packaging material having therein a PPAR-γ agonist and a label indicating a use of the agonist for one of the instant therapeutic or prophylactic methods.

Figure 1A:
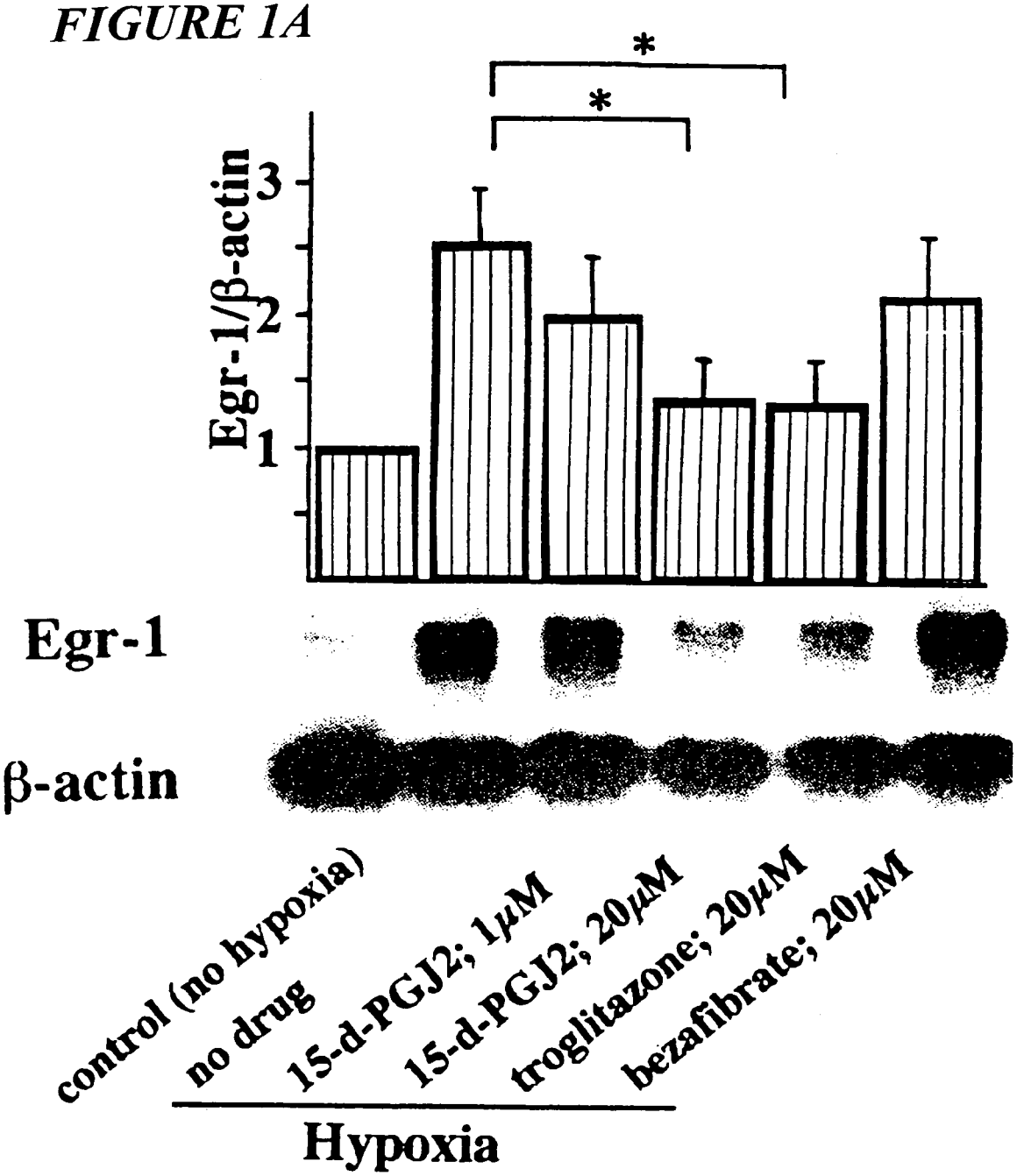
FIGS. 1A–1C

Effects of PPAR-γ activators on Egr-1 expression in hypoxic mononuclear phagocytes. In all groups except the control (no hypoxia) group, cells were exposed to hypoxia for 30 minutes after treatment of 15-d-$PGJ_2$, troglitazone or bezafibrate for 6 hours. (a) Effect of 15-d-$PGJ_2$, troglitazone or bezafibrate on Egr-1 mRNA levels, analyzed by Northern blotting with β-actin as a control. A representative blot is shown. Quantitative densitometric data from multiple experiments (n=5 for each group) are expressed as Egr-1/β-actin mRNA levels relative to the hypoxia-negative control. Data are shown as mean±standard error of the mean; *p<0.05. (b) Effect of 15-d-$PGJ_2$, troglitazone or bezafibrate on Egr-1 protein expression, analyzed by Western blotting, with another transcription factor (Sp-1) blotted as a control. A representative blot is shown. Quantitative densitometric data (expressed as Egr-1/Sp-1 levels relative to the no hypoxia control) from multiple experiments (n=8 for each group) are shown as mean±standard error of the mean; *p<0.05. (c) Electrophoretic mobility gel shift assay was performed with a $^{32}$P-labeled consensus probe for Egr on nuclear extracts. Lane 1 was loaded solely with buffer containing free $^{32}$P-labeled Egr probe. Lane 2, nuclear extract from untreated (non-hypoxic) cells; lane 3, nuclear extract from hypoxic cells without any pretreatment; lane 4, nuclear extract from hypoxic cells pretreated with 1 μM 15-d-$PGJ_2$; lane 5, nuclear extract from hypoxic cells pretreated with 20 μM 15-d-$PGJ_2$; lane 6, nuclear extract from hypoxic cells pretreated with 20 μM troglitazone; lane 7, nuclear extract from hypoxic cells pretreated with 20 μM bezafibrate; lane 8, nuclear extract from hypoxic cells without pretreatment mixed with anti-Egr-1 antibody, or a 100-fold molar excess of unlabeled consensus Egr (lane 9) prior to loading. The lower arrow indicates migration of the band corresponding to the Egr-1-DNA complex. The upper arrow pinpoints the location of an. Egr-DNA-binding species with retarded migration (supershift band) in the presence of an anti-mouse Egr-1 IgG.

FIG. 2A-2D

Induction of Egr-1 in murine lungs exposed to ischemia/reperfusion. Lung samples were either taken from naive animals (untreated), those whose hilum had been cross-clamped for 1 hour (ischemia), or those reperfused for the indicated duration following 1 hour of ischemia. (a) Effect of ischemia/reperfusion duration on Egr-1 mRNA levels. Northern blots of total mRNA were probed for Egr-1 and β-actin as a control. Quantitative densitometric data (expressed as Egr-1/β-actin mRNA levels relative to untreated lung) from multiple experiments (n=5 for each time point) are shown as mean±standard error of the mean; *p<0.05. (b) Effect of ischemia/reperfusion duration on Egr-1 protein expression. Western blotting for Egr-1 or Sp-1 (as control) is shown. Quantitative densitometric data (expressed as Egr-1/Sp-1 levels relative to untreated lung) from multiple experiments (n=5 for each time point) are shown as mean±standard error of the mean; *p<0.05. (c and d) Confocal microscopic localization of Egr-1 antigen expression. Representative sections of an untreated naive lung (c) or a lung that had been cross-clamped at the hilum for 1 hour and then reperfused for 1 hour (d), double-immunostained with an anti-Egr-1 antibody (with a secondary rhodamine-conjugated IgG) and a FITC-conjugated anti-macrophage antibody. Merged images appear yellow at sites of co-localization (color data not shown). (d) Black and white images corresponding to merged images above. Marker bar=5 μm.

Figure 3A:
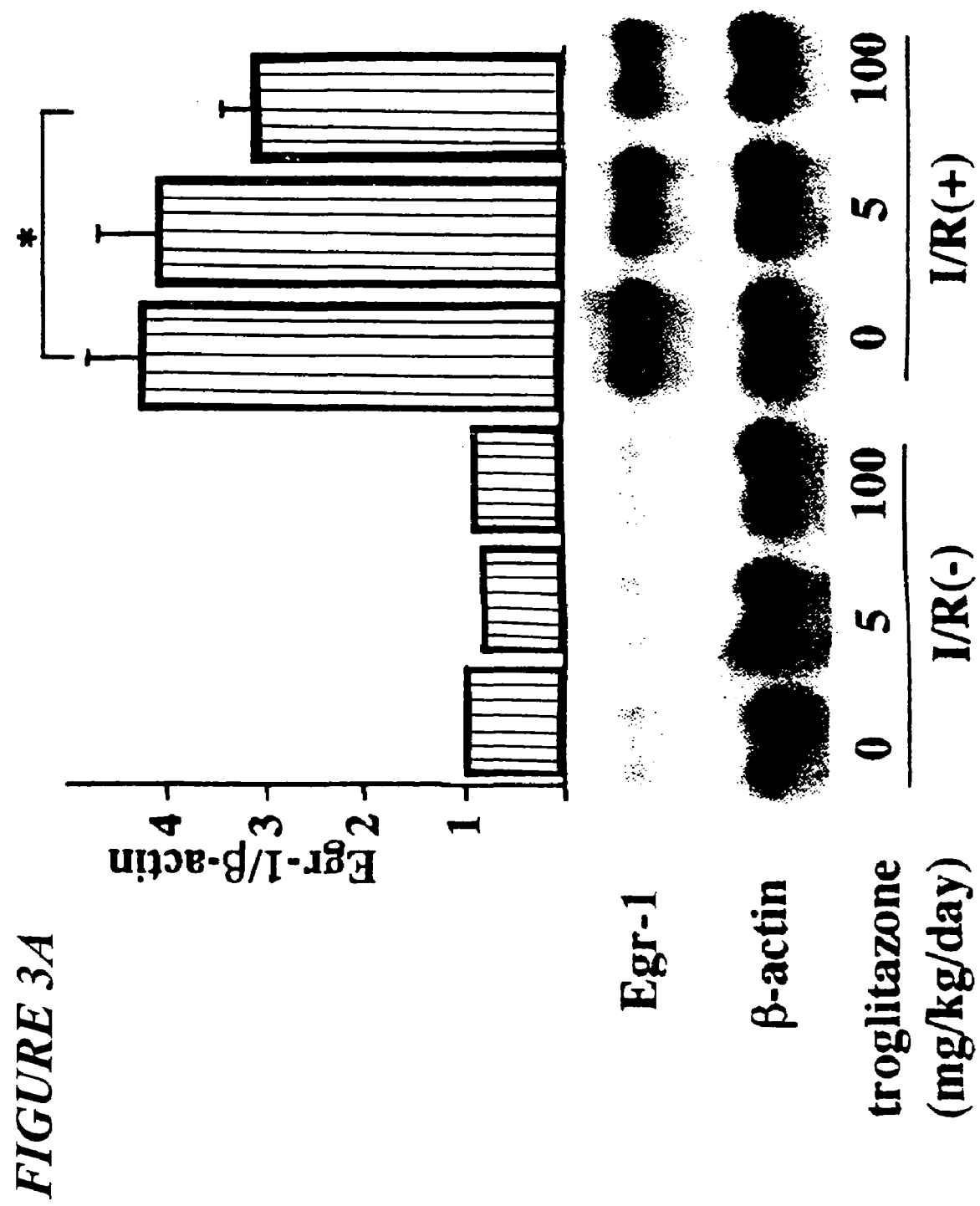
Figure 3B:
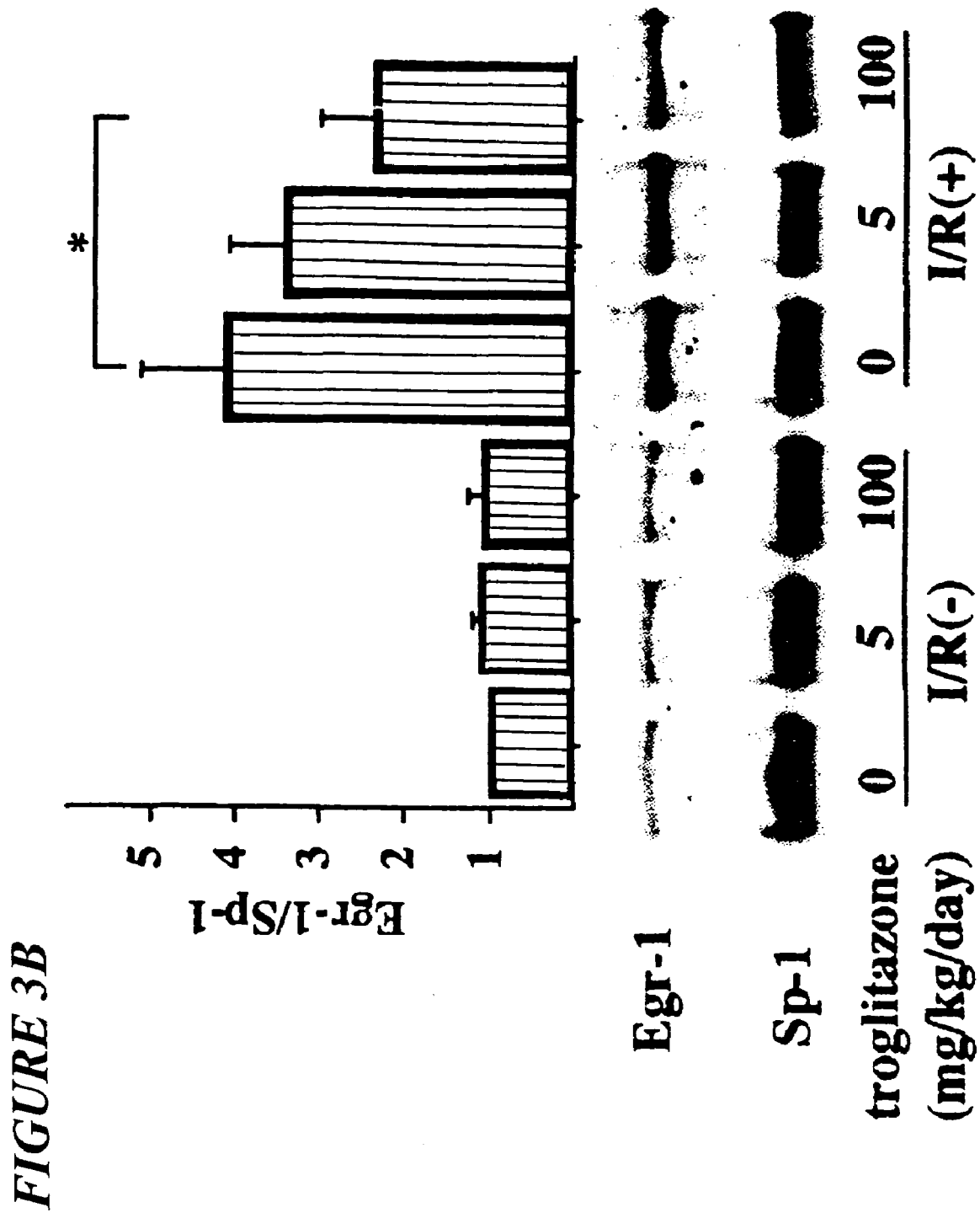

FIGS. 3A and 3B

Inhibitory effects of troglitazone on Egr-1 expression in the murine lung ischemia/reperfusion model. 0, 5 or 100 mg/kg/day of troglitazone was gavaged orally for 7 days, followed by the ischemia/reperfusion procedure wherein lungs were cross-clamped at the hilum for 1 hour, reperfused for 1 hour, and then excised. (a) Effect of troglitazone on Egr-1. mRNA levels, analyzed by Northern blotting with β-actin as a control. A representative blot is shown. Quantitative densitometric data (expressed as Egr-1/β-actin mRNA levels relative to untreated lung) from multiple experiments (n=5 for each group) are shown as mean±standard error of the mean; *p<0.05. (b) Effect of troglitazone on Egr-1 protein expression, analyzed by Western blotting, with Sp-1 as a control. A representative blot is shown. Quantitative densitometric data (expressed as Egr-1/Sp-1 levels relative to untreated lung) from multiple experiments (n=5 for each group) are shown as mean±standard error of the mean; *p<0.05.

FIGS. 4A–4F

Effects of troglitazone on lung function and gene expression in the murine lung ischemia/reperfusion model. Lungs were evaluated either in situ, or after troglitazone was gavaged orally for 7 days, followed by the ischemia/reperfusion procedure wherein lungs were cross-clamped at the hilum for 1 hour and then reperfused for 3 hours. For all experiments, data are shown as mean±standard error of the mean; *p<0.05. (a) Effects on pulmonary gas exchange, evaluated as arterial oxygenation, measured 5 minutes following circulatory exclusion of the contralateral nonclamped lung (n=6, for each group). Mice were ventilated with room air throughout the post-ischemia/reperfusion period. (b) Effects on pulmonary graft neutrophil sequestration, measured by myeloperoxidase activity assay (n=6, for each group). (c) Effects on graft IL-1β mRNA expression, analyzed by Northern blotting with β-actin as a control. A representative blot is shown, with quantitative results based on densitometric analysis of the 5 experiments (data are expressed as IL-1β/β-actin mRNA levels relative to untreated lung) (d) Effects on MCP-1 mRNA expression (n=5, for each group). (e) Effects on MIP-2 mRNA expression (n=5, for each group). (f) Effects on mice survival. Survival was recorded at 1 hour after ligation of the contralateral nonclamped pulmonary artery (n=10, for each group). This experimental cohort was completely separate from the other cohorts studied, because of the potential negative impact of phlebotomy on survival, and the variable duration of survival.

DETAILED DESCRIPTION OF THE INVENTION

Definitions

"Administering" an agent can be effected or performed using any of the various methods and delivery systems known to those skilled in the art. The administering can be performed, for example, intravenously, orally, nasally, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

"Agents" include, but are not limited to, small molecules, proteins, nucleic acids, carbohydrates, lipids and any other molecules or compounds.

"Agonist" means an agent which, when interacting, either directly or indirectly, with a biologically active molecule(s) (e.g. an enzyme or a receptor) causes an increase in the biological activity thereof. "Antagonist" means an agent which, when interacting, either directly or indirectly, with a biologically active molecule(s) (e.g. an enzyme or a receptor) causes a decrease in the biological activity thereof.

"Antibody" shall include, by way of example, both naturally occurring and non-naturally occurring antibodies. Specifically, this term includes polyclonal and monoclonal antibodies, and fragments thereof. Furthermore, this term includes chimeric antibodies and wholly synthetic antibodies, and fragments thereof.

"Cell-free system" includes, without limitation, the components of a cell, other than an intact cell membrane, required for gene expression. Such components include, for example, genomic DNA, RNA polymerase, nucleotides, and other cellular components mediating transcription and translation of genes. In one example, a cell-free system comprises whole cell extract. In another example, a cell-free system comprises whole cell extract from which cellular organelles have been removed.

"Central nervous system" means all structures within the dura mater. Such structures include, but are not limited to, the brain and spinal cord.

"Egr-1 expression" means the transcription and/or translation of the Egr-1 gene, and/or the localization of Egr-1 to a site within a cell subsequent to its translation.

"Inhibiting" the expression of Egr-1 includes either lessening the degree to which the Egr-1 is expressed (e.g., preventing such expression entirely).

"Inhibiting the onset" of a disorder means either lessening the likelihood of the disorder's onset, or preventing the onset of the disorder entirely. In the preferred embodiment, inhibiting the onset of a disorder means preventing its onset entirely.

"Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996–1997, Roche Molecular Systems, Inc., Branchburg, N.J., USA).

"PPAR-γ agonist" means an agent which, when interacting directly or indirectly with PPAR-γ, increases the biological activity of PPAR-γ (e.g., the ability of PPAR-γ to inhibit Egr-1 expression). PPAR-γ agonists include, but are not limited to, glitazones (such as troglitazone, rosiglitazone, pioglitazone, ciglitazone, englitazone and darglitazone), 15 deoxy-$\Delta^{12,14}$-prostaglandin $J_2$ and analogs, derivatives, and pharmaceutically acceptable salts thereof.

"Prophylactically effective amount" means an amount sufficient to inhibit the onset of a disorder or a complication associated with a disorder in a subject.

"Subject" shall mean any animal, such as a primate, mouse, rat, guinea pig or rabbit. In the preferred embodiment, the subject is a human.

"Therapeutically effective amount" means an amount sufficient to treat a subject afflicted with a disorder or a complication associated with a disorder.

"Treating" a disorder shall mean slowing, stopping or reversing the progression of the disorder and/or a related complication. In the preferred embodiment, "treating" a disorder means reversing the disorder's progression, ideally to the point of eliminating the disorder itself. As used herein in this context, "ameliorating" and "treating" are equivalent.

Embodiments of the Invention

This invention provides a first method for determining whether an agent increases PPAR-γ-mediated inhibition of Egr-1 expression comprising
  (a) (i) contacting the agent with a cell-free system which comprises PPAR-γ, permits the expression of Egr-1 and permits the inhibition of such expression in the presence of a PPAR-γ agonist, and (ii) subjecting the cell-free system to a stimulus known to increase Egr-1 expression in a cell, wherein steps (i) and (ii) are performed concurrently or in sequence;
  (b) determining the amount of Egr-1 expression in the cell-free system;
  (c) comparing the amount of Egr-1 expression determined in step (b) to the amount of Egr-1 expression observed in the absence of the agent, wherein the amount of Egr-1 expression in the absence of the agent being greater than that in the presence of the agent indicates that the agent inhibits Egr-1 expression; and
  (d) comparing the amount of Egr-1 expression determined in step (b) with the amount of Egr-1 expression observed in the presence of the agent under conditions known to inhibit PPAR-γ activation, wherein the amount of Egr-1 expression in the presence of the agent under such conditions being greater than that determined in step (b) indicates that the agent increases PPAR-γ-mediated inhibition of Egr-1 expression.

In one embodiment of the first method, the cell-free system comprises cellular components from a human cell. In another embodiment, the cell-free system comprises cellular components from a mononuclear phagocyte, a lymphocyte, a neutrophil, an endothelial cell, an epithelial cell, a smooth muscle cell, a neuron or a hepatocyte.

The stimulus known to increase Egr-1 expression in a cell can be any stimulus known to have such an effect. In one embodiment, the stimulus is hypoxia.

Determining the amount of Egr-1 expression can be performed according to routine methods. In one embodiment, determining the amount of Egr-1 expression comprises determining the amount of Egr-1 protein present in the cell-free system. In another embodiment, determining the amount of Egr-1 expression comprises determining the amount of Egr-1 mRNA present in the cell-free system. In a further embodiment, determining the amount of Egr-1 expression comprises determining the amount of Egr-1 protein present in the cell-free system which binds to a nucleic acid comprising an Egr-1 binding site (e.g., as accomplished via gel shift assay).

Conditions known to inhibit PPAR-γ activation include, for example, contact with a PPAR-γ antagonist or an anti-PPAR-γ antibody. Methods of using antagonists and antibodies in assays are routine in the art.

In the preferred embodiment of the first method, the cell-free system is a nuclear extract, the stimulus is hypoxia, determining the amount of Egr-1 expression in the cell-free system is performed by gel shift assay, and the conditions known to inhibit PPAR-γ activation are the presence of an anti-PPAR-γ antibody.

This invention also provides a second method for determining whether an agent increases PPAR-γ-mediated inhibition of Egr-1 expression in a cell comprising
  (a) (i) contacting the agent with the cell, and (ii) subjecting the cell to a stimulus known to increase Egr-1 expression in a cell, wherein steps (i) and (ii) are performed concurrently or in sequence;
  (b) determining the amount of Egr-1 expression in the cell;
  (c) comparing the amount of Egr-1 expression determined in step (b) to the amount of Egr-1 expression observed in the cell in the absence of the agent, wherein the amount of Egr-1 expression in the absence of the agent being greater than that in the presence of the agent indicates that the agent inhibits Egr-1 expression in the cell; and
  (d) comparing the amount of Egr-1 expression determined in step (b) with the amount of Egr-1 expression observed in the presence of the agent and under conditions known to inhibit PPAR-γ activation, wherein the amount of Egr-1 expression in the presence of the agent under such conditions being greater than that determined in step (b) indicates that the agent increases PPAR-γ-mediated inhibition of Egr-1 expression.

In one embodiment of the second method, the cell is a human cell. In another embodiment, the cell is a mononuclear phagocyte, a lymphocyte, a neutrophil, an endothelial cell, an epithelial cell, a smooth muscle cell, a neuron or a hepatocyte. In a further embodiment, the cell is a murine cell, a rat cell, a feline cell, a canine cell, a porcine cell, a primate cell and a human cell. Cells can be derived, for example, from cardiac, lung, nervous, renal, or hepatic tissue.

The stimulus known to increase Egr-1 expression in a cell can be any stimulus known to have such an effect. In one embodiment, the stimulus is hypoxia or administration of an inflammatory agent.

In the second method, determining the amount of Egr-1 expression can be performed according to routine methods. In one embodiment, determining the amount of Egr-1 expression comprises determining the amount of Egr-1 protein present in the cell. In another embodiment, determining the amount of Egr-1 expression comprises determining the amount of Egr-1 mRNA present in the cell. In another embodiment, determining the amount of Egr-1 expression comprises determining the amount of Egr-1 protein present in the cell which binds to a nucleic acid comprising an Egr-1 binding site. Additionally, conditions known to inhibit PPAR-γ activation include, for example, contact with a PPAR-γ antagonist or an anti-PPAR-γ antibody.

In the preferred embodiment of the second method, the cell is a mononuclear phagocyte, the stimulus is hypoxia, and determining the amount of Egr-1 expression in the cell is performed by determining the amount of Egr-1 mRNA present in the cell.

This invention further provides a third method for determining whether an agent increases PPAR-γ-mediated inhibition of Egr-1 expression in a subject's cells comprising (a) (i) administering the agent to a non-human subject, and (ii) subjecting the subject to a stimulus known to increase Egr-1 expression in the subject's cells, wherein steps (i) and (ii) are performed concurrently or in sequence;

(b) determining the amount of Egr-1 expression in the subject's cells;

(c) comparing the amount of Egr-1 expression determined in step (b) to the amount of Egr-1 expression observed in the subject's cells in the absence of the agent, wherein the amount of Egr-1 expression in the absence of the agent being greater than that in the presence of the agent indicates that the agent inhibits Egr-1 expression in the subject's cells; and (d) comparing the amount of Egr-1 expression determined in step (b) with the amount of Egr-1 expression observed in the presence of the agent under conditions known to inhibit PPAR-γ activation, wherein the amount of Egr-1 expression in the presence of the agent under such conditions being greater than that determined in step (b) indicates that the agent increases PPAR-γ-mediated inhibition of Egr-1 expression.

In one embodiment of the third method, determining the amount of Egr-1 expression comprises determining the amount of Egr-1 protein present in the subject's cells. In another embodiment, determining the amount of Egr-1 expression comprises determining the amount of Egr-1 mRNA present in the subject's cells. In another embodiment, determining the amount of Egr-1 expression comprises determining the amount of Egr-1 protein present in the subject's cells which binds to a nucleic acid comprising an Egr-1 binding site.

In the third method, the conditions known to inhibit PPAR-γ activation include, without limitation, contact with a PPAR-γ antagonist or an anti-PPAR-γ antibody.

Additionally, stimulus known to increase Egr-1 expression in a cell can be any stimulus known to have such an effect. In one embodiment, the stimulus is artificially-induced ischemia. In another embodiment, the stimulus is ischemia and reperfusion. In a further embodiment, the stimulus is mechanical injury, or the administration of an inflammatory agent.

In the third method, the subject's cells in which inhibition of Egr-1 expression occurs can be, for example, cardiac cells, vascular cells, neuronal cells, hepatic cells, lung cells and renal cells. Further, the subject is preferably a mammal, such as a mouse, a rat, a cat, a dog or a primate.

In the preferred embodiment of the third method, the subject's cells are mononuclear phagocytes, the stimulus is ischemia, and determining the amount of Egr-1 expression in the subject's cells is performed by determining the amount of Egr-1 mRNA present in the subject's cells.

This invention provides a method for inhibiting the onset of atherosclerosis in a transplanted organ comprising administering to the organ recipient a prophylactically effective amount of a PPAR-γ agonist, thereby inhibiting the onset of atherosclerosis in the transplanted organ. This invention also provides a method for inhibiting the onset of atherosclerosis in a transplanted organ comprising administering to the organ donor, prior to transplantation of the organ to a recipient, a prophylactically effective amount of a PPAR-γ agonist, thereby inhibiting the onset of atherosclerosis in the transplanted organ.

In one embodiment of each of the instant methods, the PPAR-γ agonist is a glitazone such as rosiglitazone or piaglitazone. In another embodiment, the PPAR-γ agonist is 15 deoxy-$\Delta^{12,14}$-prostaglandin $J_2$.

In a further embodiment of these methods, the PPAR-γ agonist is administered to the organ recipient prior to transplantation. Alternatively, the PPAR-γ agonist is administered to the organ recipient during transplantation, or after transplantation. In another embodiment, the PPAR-γ agonist is administered to the organ recipient prior to, during and after transplantation. In the preferred embodiment of these instant methods, the organ donor and organ recipient are human.

This invention also provides numerous methods of inhibiting the onset of a disorder and/or a complication associated with a disorder in a subject by administering to the subject a prophylactically effective amount of a PPAR-γ agonist, thereby inhibiting the onset of the disorder or the complication associated with the disorder in the subject. Disorders and complications associated with a disorder include, but are not limited to, an inflammatory disorder-related complication (e.g., tissue injury); an ischemia-related complication (e.g., tissue injury); an ischemia/reperfusion-related complication (e.g., tissue injury); a multiple organ system dysfunction-related complication (e.g., renal failure, altered mentation, tissue injury, hypotension or fever); acute respiratory distress syndrome; a central nervous system disorder; a multiple sclerosis-related complication (e.g., demyelination); stroke; a heart attack; vascular disease; atherosclerosis; and a sepsis-related complication (e.g., low blood pressure, hypotension, or tissue injury).

This invention further provides numerous methods of treating a subject afflicted with a disorder or a complication associated with a disorder by administering to the subject a therapeutically effective amount of a PPAR-γ agonist, thereby treating the subject. Disorders and complications (those listed above) associated with a disorder include, but are not limited to, an inflammatory disorder; ischemia; an ischemia/reperfusion-related complication; multiple organ system dysfunction; acute respiratory distress syndrome; a central nervous system disorder; multiple sclerosis; Alzheimer's disease; stroke; vascular disease; atherosclerosis; sepsis; a heart attack; a burn injury; and a crush injury.

Determining a prophylactically or therapeutically effective amount of PPAR-γ agonist for use in the instant invention can be done based on animal data using routine computational methods. In one embodiment, the effective amount contains between about 0.1 mg/subject/day and 500 mg/subject/day of agonist. In another embodiment, the effective amount contains between about 1 mg/subject/day and 100 mg/subject/day of agonist. In a further embodiment, the effective amount contains between about 5 mg/subject/ day and 50 mg/subject/day of agonist. In a further embodiment, the effective amount contains about 4–8 mg/subject/day of rosiglitazone. In still a further embodiment, the effective amount contains about 15–45 mg/subject/day of piaglitazone.

In each of the instant prophylactic and therapeutic methods, the preferred subject is a human. Also, in one embodiment of each of the instant prophylactic and therapeutic methods, the PPAR-γ agonist is a glitazone such as rosiglitazone or piaglitazone, or 15 deoxy-$\Delta^{12,14}$-prostaglandin $J_2$.

This invention also provides a method for inhibiting the onset of a complication (e.g., complement activation, blood coagulation, or the release of inflammatory or cytotoxic mediators) in a subject resulting from a procedure wherein the subject's body fluid comes into contact with a foreign surface, comprising administering to the subject a prophylactically effective amount of a PPAR-γ agonist, thereby inhibiting the onset of the complication. Body fluids include, for example, blood, plasma, lymph, and cerebrospinal fluid.

This invention further provides a method for inhibiting the onset of a complication (e.g., complement activation, blood coagulation, the release of inflammatory or cytotoxic mediators, impaired gas exchange, neurological dysfunction, or disseminated intravascular coagulation) in a subject resulting from the administration of an extracorporeal oxygenation procedure to the subject, comprising administering to the subject a prophylactically effective amount of a PPAR-γ agonist, thereby inhibiting the onset of the complication.

This invention further provides a method for inhibiting the onset of a complication (e.g., complement activation, blood coagulation, or the release of inflammatory or cytotoxic mediators, impaired gas exchange, neurological dysfunction, disseminated intravascular coagulation or myocardial infarction) in a subject resulting from cardio-pulmonary bypass surgery, comprising administering to the subject a prophylactically effective amount of a PPAR-γ agonist, thereby inhibiting the onset of the complication.

In each of the instant methods for inhibiting the onset of a complication in a subject resulting from a procedure, the PPAR-γ agonist can be administered to the subject prior to the procedure, during the procedure, after the procedure, or prior to, during and after the procedure.

This invention also provides a method for treating a subject afflicted with a complication (as set forth above) resulting from an extracorporeal oxygenation procedure, comprising administering to the subject a therapeutically effective amount of a PPAR-γ agonist, thereby treating the subject. This invention also provides a method for ameliorating a complication (as set forth above) in a subject resulting from cardio-pulmonary bypass surgery, comprising administering to the subject a therapeutically effective amount of a PPAR-γ agonist, thereby ameliorating the complication.

This invention also provides a method for inhibiting the metastasis of a cancerous cell, comprising contacting the cell with an amount of a PPAR-γ agonist effective to inhibit metastasis of the cancerous cell. In one embodiment, the cancerous cell is a colon cancer cell, a breast cancer cell, a lung cancer cell, a lymphatic cancer cell, a renal cancer cell or a skin cancer cell. In the preferred embodiment, the cancer cell is a human cancer cell. The PPAR-γ agonist can be, for example, a glitazone such as rosiglitazone or piaglitazone. In another embodiment, the PPAR-γ agonist is 15 deoxy-$\Delta^{12,14}$-prostaglandin $J_2$.

This invention also provides a method for treating a subject afflicted with cancer, comprising administering to the subject a therapeutically effective amount of a PPAR-γ agonist, thereby treating the subject. In one embodiment, the cancer is colon cancer, breast cancer, lung cancer, lymphatic cancer, renal cancer or skin cancer.

This invention also provides an article of manufacture comprising a packaging material having therein a PPAR-γ agonist and a label indicating a use of the agonist for treating, or inhibiting the onset of, atherosclerosis in a transplanted organ.

This invention further provides numerous other articles of manufacture comprising a packaging material having therein a PPAR-γ agonist and a label indicating a use of the agonist for inhibiting the onset of a disorder, or a complication associated with a disorder. Such disorders and complications associated with a disorders include, but are not limited to, those as set forth above in connection with the instant prophylactic methods.

This invention still further provides numerous articles of manufacture comprising a packaging material having therein a PPAR-γ agonist and a label indicating a use of the agonist for treating a disorder, or a complication associated with a disorder. Disorders and complications associated with a disorder include those set forth above in connection with the instant therapeutic methods.

This invention also provides an article of manufacture comprising a packaging material having therein a PPAR-γ agonist and a label indicating a use of the agonist for treating, or inhibiting the onset of, a complication resulting from a procedure on a subject wherein the subject's body fluid comes into contact with a foreign surface. Such procedures include, but are not limited to, performance of an extracorporeal oxygenation procedure, and cardio-pulmonary bypass surgery.

This invention also provides an article of manufacture comprising a packaging material having therein a PPAR-γ agonist and a label indicating a use of the agonist for inhibiting the metastasis of a cancerous cell.

Finally, this invention provides an article of manufacture comprising a packaging material having therein a PPAR-γ agonist and a label indicating a use of the agonist for treating a subject afflicted with cancer.

In each of the instant articles of manufacture, the PPAR-γ agonist includes, but is not limited to, a glitazone such as rosiglitazone or piaglitazone, and 15 deoxy-$\Delta^{12,14}$-prostaglandin $J_2$.

This invention is illustrated in the Experimental Details section that follows. This section is set forth to aid in an understanding of the invention but is not intended to, and should not be construed to, limit in any way the invention as set forth in the claims which follow thereafter.

Experimental Details

A. Synopsis

The peroxisome proliferator-activated receptor (PPAR) is a nuclear receptor whose activation regulates both metabolism and inflammation. Recent data indicate that the zinc finger transcription factor early growth response gene-1 (Egr-1) acts as a master switch for the inflammatory response in ischemic vessels. The instant experiments demonstrate that activation of endogenous PPAR-Y inhibits induction of Egr-1. Egr-1 is rapidly induced in murine lungs following ischemia-reperfusion, as well as in alveolar mononuclear phagocytes deprived of oxygen as an ischemic model. In vitro, the natural PPAR-γ ligand (15-deoxy-$\Delta^{12,14}$-prostaglandin$J_2$) and a PPAR-γ activator (troglitazone) but not a PPAR-α activator (bezafibrate) strikingly diminished Egr-1 mRNA and protein expression and nuclear DNA binding activity corresponding to Egr-1. In vivo, treatment with troglitazone prior to ischemia prevented induction of Egr-1 and its target genes such as interleukin-1β, monocyte chemotactic protein-1 (MCP-1), and macrophage inflammatory protein-2 (MIP-2). As a consequence of PPAR-γ activation, pulmonary leukostasis was decreased, and oxygenation and overall survival were improved. Activation of PPAR-γ suppresses activation of Egr-1 and its inflammatory gene targets and provides potent protection against ischemic pulmonary injury. These data show a mechanism whereby PPAR-γ activation decreases tissue inflammation in response to an ischemic insult.

B. Materials and Methods

Cell culture and induction of hypoxia. A rat alveolar macrophage cell line (NR8383) was obtained from the ATCC (Manassas, Va.), and cells were grown to 70% confluence in Ham's F-12K medium containing 15% heat-inactivated fetal bovine serum. Cells were made quiescent by serum starvation (0.2%, fetal bovine serum) for 24 hours. The PPAR-γ ligands were obtained from the following sources: troglitazone was provided by Sankyo Pharmaceutical Co. (Tokyo, Japan); and 15-d-PGJ$_2$ was purchased from Cayman Chemical Co. (Ann Arbor, Mich.). The PPAR-α ligand bezafibrate was obtained from Sigma Chemical Co. (St. Louis. Mo.). These PPAR ligands were dissolved in minute quantities of DMSO (final concentration 0.005%). PPAR ligands were added 6 hours prior to induction of hypoxia. Using an environmental chamber described previously (Yan, 1999), cells were subjected to 30 minutes hypoxia (pO$_2$ in the medium ~12–14 torr. This time was chosen because it has previously been shown that this is the time of maximal Egr-1 expression in hypoxic macrophages. Cells subjected to hypoxia were placed in medium pre-equilibrated with the hypoxic gas mixture just prior to placement in the environmental chamber. Thus, cultures were immersed immediately in the oxygen-deprived environment at the time of medium change, coinciding with time of placement in the chamber.

Murine ischemia/reperfusion model. C57BL6/J mice (male, 12–15 weeks old) purchased from Jackson Laboratories (Bar Harbor, Me.) were used in these experiments according to a protocol approved by the Institutional Animal Care and Use Committee at Columbia University, in accordance with guidelines of the American Association for the Accreditation of Laboratory Animal Care.

Troglitazone was administered to mice by oral gavage (0.1 mL/mouse) for 7 days at doses of 0, 5, and 100 mg/kg/day, prepared as a suspension in 0.5% methylcellulose solution. For control experiments, methylcellulose solution alone was used for gavage (these experiments are referred to as "vehicle" controls). The ischemia/reperfusion stress followed on day 8. Animals were initially anesthetized intraperitoneally with 0.1 mg/g mouse weight (ketamine) and 0.01 mg/g mouse weight (xylazine), followed by intraperitoneal infusion of one third of the initial dose per hour controlled. After ensuring appropriate depth of anesthesia, mice were intubated via tracheotomy and placed on a Harvard ventilator (tidal volume=0.5 mL, respiratory rate=120/minute) with room air, followed by bilateral thoracotomy. The left hilum was cross-clamped for 1 hour followed by 30 minutes to 3 hours reperfusion (exact times are identified in the Results and Brief Description of the Figures). Lung specimens were excised just after reperfusion for Northern or Western blot analysis. Survival was measured 1 hour after circulatory exclusion of the nonoperated lung (by ligating the right hilum), which was performed after both the ischemic and reperfusion (3 hours) periods had elapsed. In a separate series of experiments, lung function was ascertained by arterial blood gas analysis in mice that survived for 5 minutes after right hilar ligation.

Northern blotting. Total RNA (20 μg/lane) obtained from cultured mononuclear phagocytes or murine lung tissue after homogenization was extracted using Trizol (Life Technologies, Rockville, Md.) and subjected to electrophoresis in 0.8% agarose-formaldehyde gels, followed by capillary transfer to Duralon-UV membranes (Stratagene, La Jolla, Calif.). Membranes hybridized with $^{32}$P-labeled cDNA probes for Egr-1, IL-1β, MCP-1, or MIP-2 (Yan, 2000) were subsequently exposed to Kodak Biomax film at −80° C. Membranes were then stripped and rehybridized with radiolabeled β-actin cDNA as a control for RNA loading and transfer efficiency.

Western blotting. Extracts of cultured mononuclear phagocytes or murine lung tissue homogenate were mixed with a protease inhibitor cocktail (Roche Molecular Biochemicals, Mannheim, Germany), and 20 μg of protein was loaded into each lane of a SDS-polyacrylamide gel (7.5%). Following application of appropriate voltage across the gel to separate proteins according to size, proteins were transferred electrophoretically to nitrocellulose membranes. Immunoblotting was performed using a primary rabbit anti-mouse Egr-1 IgG (Santa Cruz Biotechnology, Santa Cruz, Calif.) and a rabbit anti-mouse Sp-1 IgG (Santa Cruz Biotechnology). Secondary detection of sites of primary antibody deposition was accomplished using a horseradish peroxidase-conjugated goat anti-rabbit IgG (Sigma Chemical Co). Final detection of immunoreactive bands was done with the enhanced chemiluminescent Western blotting system (Amersham International, Buckinghamshire, England).

Electrophoretic mobility gel shift assay. The assay was performed on nuclear extracts from cultured mononuclear phagocytes by the method of Dignam et al. (Dignam, 1983). Probes for Egr (Santa Cruz Biotechnology) were 5' end-labeled with [$^{32}$P]ATP (3,000 Ci/mmol) using T4 polynucleotide kinase. Binding reactions were done as described (Yan, 1995), and samples were loaded directly onto nondenaturing polyacrylamide/bisacrylamide (4%) gels (10 μg of protein in each lane). Competition experiments were performed by adding a 100-fold molar excess of unlabeled Egr probe. Supershift experiments were done by pre-incubating samples with anti-mouse Egr-1 antibody (Santa Cruz Biotechnology) for 1 hour at 4° C., prior to application to the gel. Electrophoresis was performed at room temperature for 2 hours at 200 V.

Immunofluorescence. Lung tissue was harvested, washed, embedded, frozen, and sectioned into 5-μm sections with a cryostat. The sections were fixed in acetone and incubated with a rabbit polyclonal anti-rat Egr-1 antibody (1:100 dilution; Santa Cruz Biotechnology) and rhodamine-conjugated donkey anti-rabbit IgG (1:50 dilution; Santa Cruz Biotechnology). Sections were then incubated with fluorescein isothiocyanate (FITC)-conjugated rat anti-mouse macrophage antibody (F4/80; 1:20 dilution; Caltag Laboratories, Burlingame, Calif.). For confocal microscopy, antigen detection was accomplished using a Zeiss® LSM410 laser scanning confocal microscope with epifluorescent illumination (excitation wavelength 568 nm for rhodamine, 488 nm for FITC).

Myeloperoxidase assay. Tissue myeloperoxidase activity was measured as an index of graft leukocyte accumulation.

This assay was performed as previously described (Goldblum, 1985) and data are expressed as change in absorbance at 460 nm per minute.

Statistics. All statistical comparisons were done using commercially available statistical software (STAT VIEW-J 5.0, Abacus Concepts) on Macintosh G4 PowerPC computer. One way ANOVA was used to make statistical comparisons among different conditions. Survival was estimated by the Kaplan-Meier method, with differences in survival determined by log-rank analysis. Values are expressed as mean±standard error of the mean (SEM), with differences considered statistically significant when $p<0.05$.

C. Results

Figure 1B:
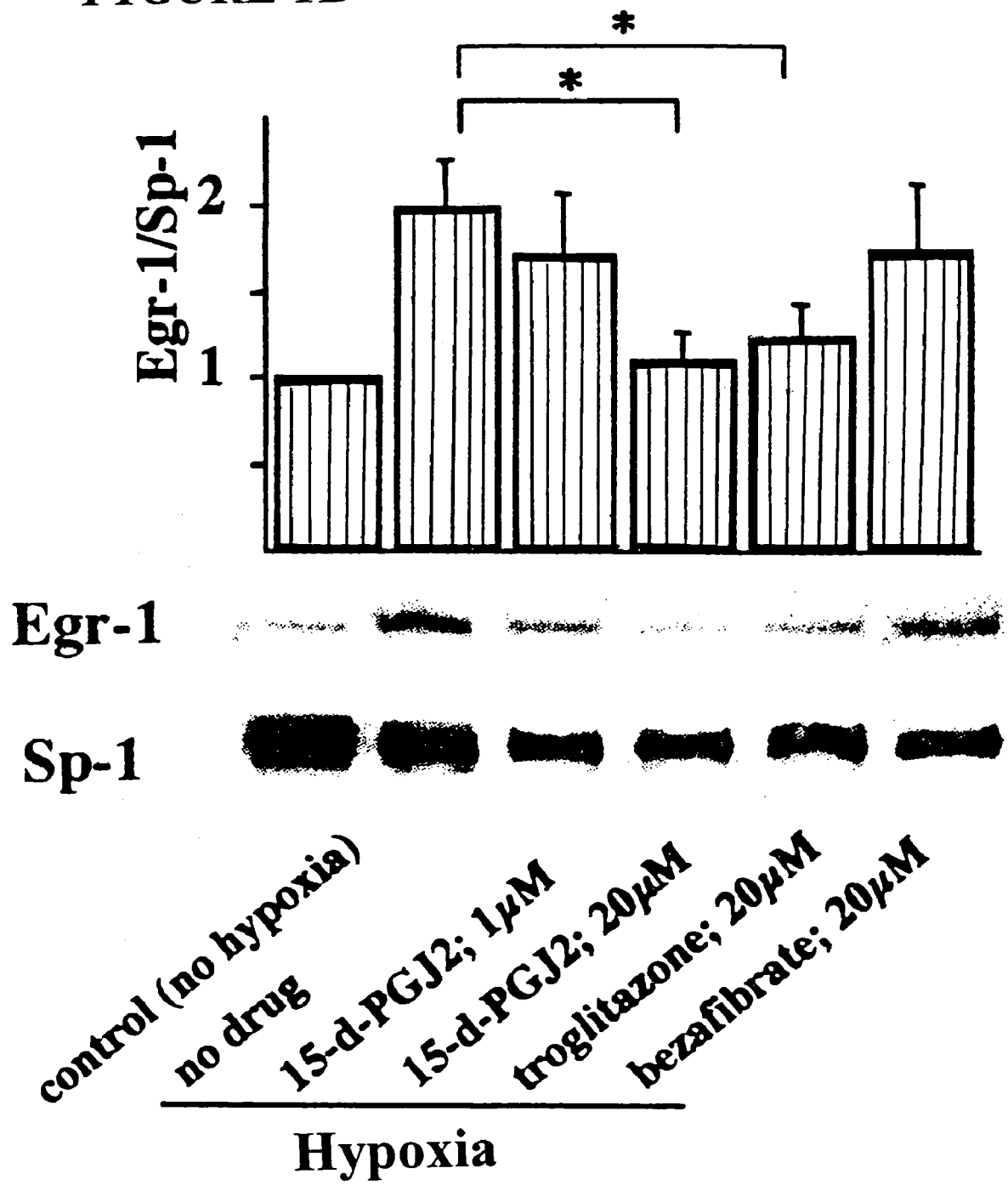
Figure 1C:

Effects of PPAR-γ Activators on Egr-1 Expression in Hypoxic Mononuclear Phagocytes The first set of experiments tested whether PPAR-γ activators could inhibit the increased expression of Egr-1 observed in hypoxic mononuclear phagocytes. Egr-1 mRNA levels measured 30 minutes after exposure to hypoxia were markedly elevated in the group of cells treated with DMSO alone as a control (FIG. 1a, lane 2). A similar degree of Egr-1 mRNA induction was noted in the group of cells treated with the PPAR-α activator, bezafibrate. However, when cells were treated with 15-d-PGJ$_2$ or troglitazone (PPAR-γ activators) but otherwise subjected to identical hypoxic procedures, Egr-1 mRNA levels were significantly reduced (FIG. 1a, lanes 4 and 5). Concordant with these observations, analyses of the expression of Egr-1 protein showed that 15-d-PGJ$_2$ or troglitazone, but not bezafibrate, significantly inhibited increased levels of Egr-1 protein detected by Western blotting after hypoxia (FIG. 1b). The effect of PPAR-γ activators to reduce expression of Egr-1 was specific, in that a related transcription factor (Sp-1) was not affected. To confirm that the measured decreases in Egr-1 mRNA and protein with PPAR-γ activators were associated with reduced Egr-1/DNA binding in nuclear extracts taken from alveolar macrophages, electrophoretic gel mobility shift assays were performed on nuclear extracts from NR8383 cells using a $^{32}$P-labeled consensus oligonucleotide probe for Egr. These experiments demonstrated that although there was no discrete gel shift band in nuclear extracts of untreated non-hypoxic cells (FIG. 1c, lane 2), a dense band was observed in nuclear extracts of both DMSO-treated (FIG. 1c, lane 3) and bezafibrate-treated (FIG. 1c, lane 7) cells obtained 30 minutes after exposure to hypoxia. In sharp contrast, pretreatment of cells with the PPAR-γ ligands 15-d-PGJ$_2$ or troglitazone virtually abrogated the gel retardation band associated with Egr-1/DNA binding (FIG. 1c, lanes 4, 5 and 6). Supershift experiments were also performed to confirm the authenticity of the DNA-binding species, responsible for retardation of electrophoretic mobility in the gel, as Egr-1. An antimouse Egr-1 antibody added to the reaction mixture caused a supershift (FIG. 1c, lane 8), indicating that the gel shift band represented DNA interaction with authentic Egr-1. Further evidence for the Egr specificity of the protein-DNA interaction was shown by competition experiments in which a 100-fold molar excess of unlabeled Egr probe obliterated the appearance of the gel shift band (FIG. 1c, lane 9).

Induction of Egr-1 in Murine Lungs Exposed to Ischemia and Reperfusion

Figure 2A:
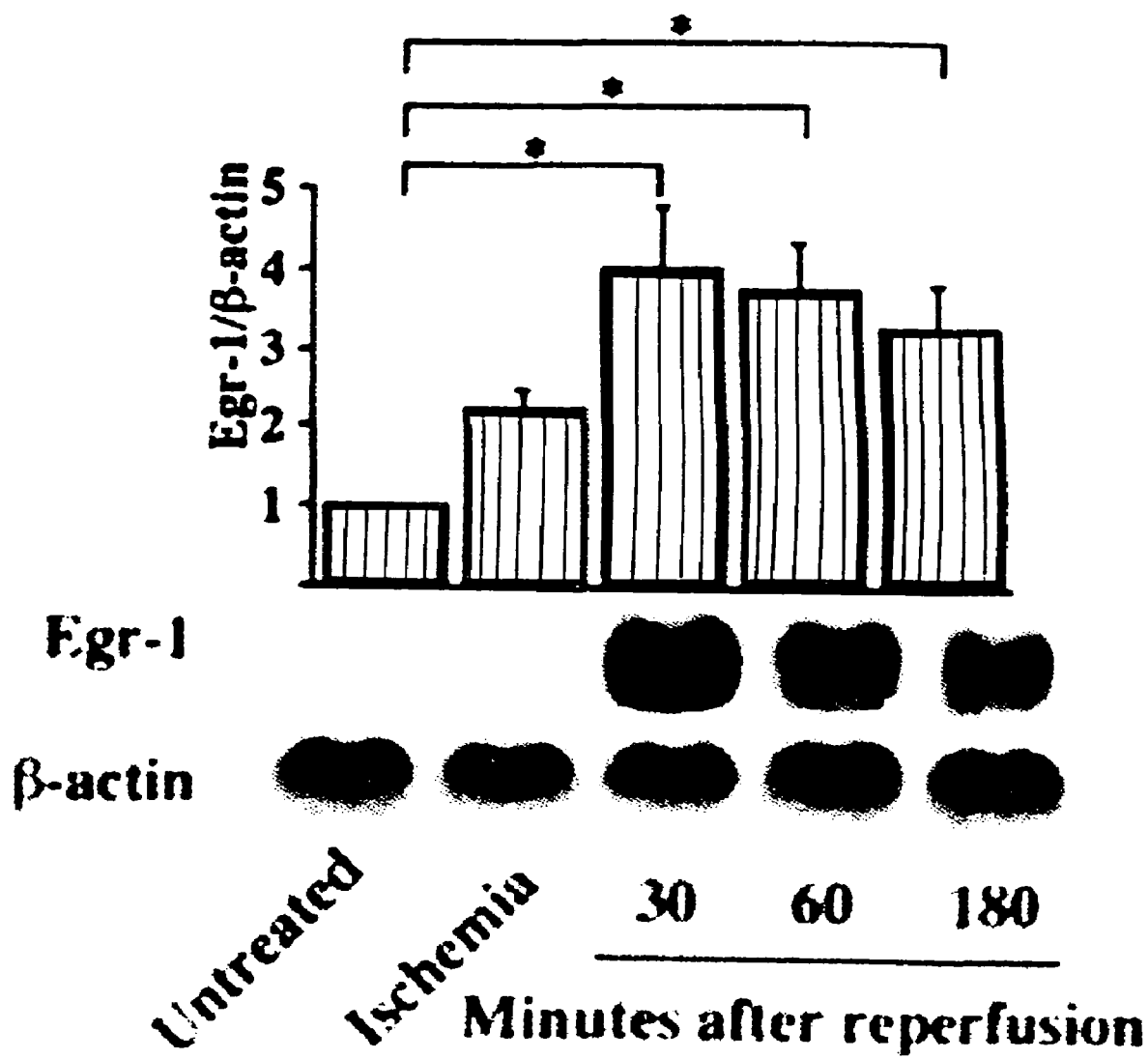
Figure 2B:
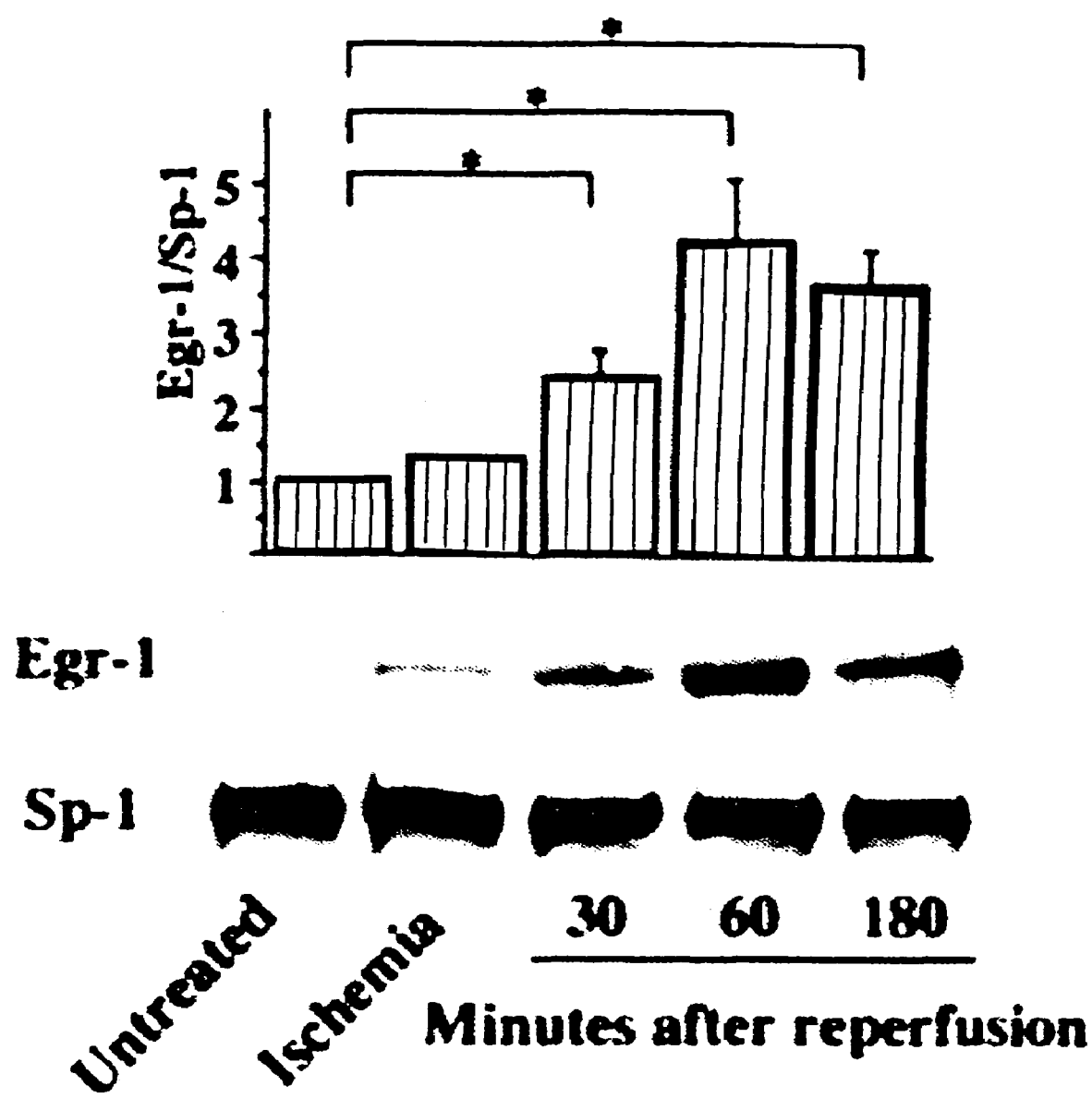

The time course of Egr-1 expression following lung ischemia was initially examined by Northern blot analysis. Clamping of the pulmonary hilum for 1 hour caused a detectable increase in the density of the band corresponding to Egr-1 mRNA, with a more pronounced increase in Egr-1 mRNA levels detected following reperfusion. Egr-1 mRNA levels peaked 30 minutes after reperfusion and subsequently tapered off, based upon densitometric analysis of multiple blots (FIG. 2a). A rapid increase in Egr-1 protein was observed along nearly the same time course with a minor rightward temporal shift, as could be expected based upon the time required to translate nascent mRNA. Peak expression of Egr-1 protein was observed at 1 hour after reperfusion (FIG. 2b). Expression of Egr-1 protein, relative to the expression of an unrelated zinc finger family transcription factor (Sp-1), was increased, based upon densitometric analysis of multiple blots.

Figure 2D:
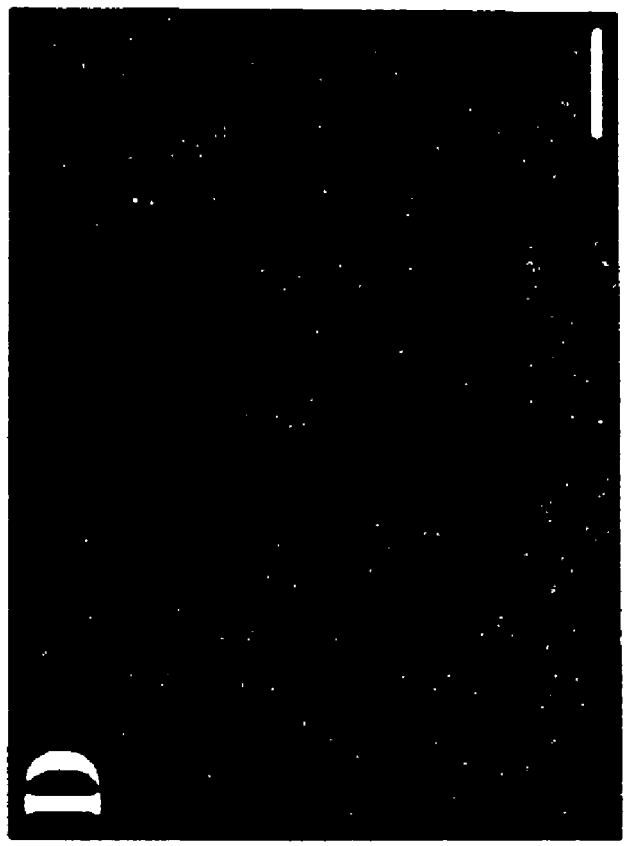
Figure 2C:

To ascertain sites of Egr-1 expression following reperfusion, immunohistochemical analysis was performed on lung tissue. Fluorescent immunohistochemistry of untreated naïve lungs indicated that Egr-1 antigen was virtually undetectable (FIG. 2c). When sections from lung tissue that had been cross-clamped at the hilum for 1 hour and then reperfused for 1 hour were subjected to the same immunostaining procedures, Egr-1 immunoreactivity was shown to be significantly increased in the medial smooth muscle as well as mononuclear phagocytes (identified by the colocalization of the fluorescence signals of rhodamine-conjugated anti-Egr-1 and FITC-conjugated F4/80) (FIG. 2d).

Effects of Troglitazone on Egr-1 Expression in Ischemic/Reperfused Murine Lungs

The next experiments tested whether a PPAR-γ agonist such as troglitazone could reduce the increased expression of Egr-1 observed in reperfused lungs. Egr-1 mRNA levels measured 1 hour after reperfusion were markedly elevated in the group of lungs from mice given vehicle alone (FIG. 3a). However, when mice were treated with troglitazone but otherwise subjected to identical ischemia/reperfusion procedures, Egr-1 mRNA levels were significantly decreased in a dose-dependent manner. Concordant with these observations, analyses of the expression of Egr-1 protein showed that troglitazone significantly inhibited increased levels of Egr-1 protein observed after ischemia/reperfusion (FIG. 3b). The effect of troglitazone to reduce Egr-1 expression was specific, in that a related transcription factor (Sp-1) was not affected.

Effects of Troglitazone on Lung Function and Leukocyte Accumulation

Figure 4A:
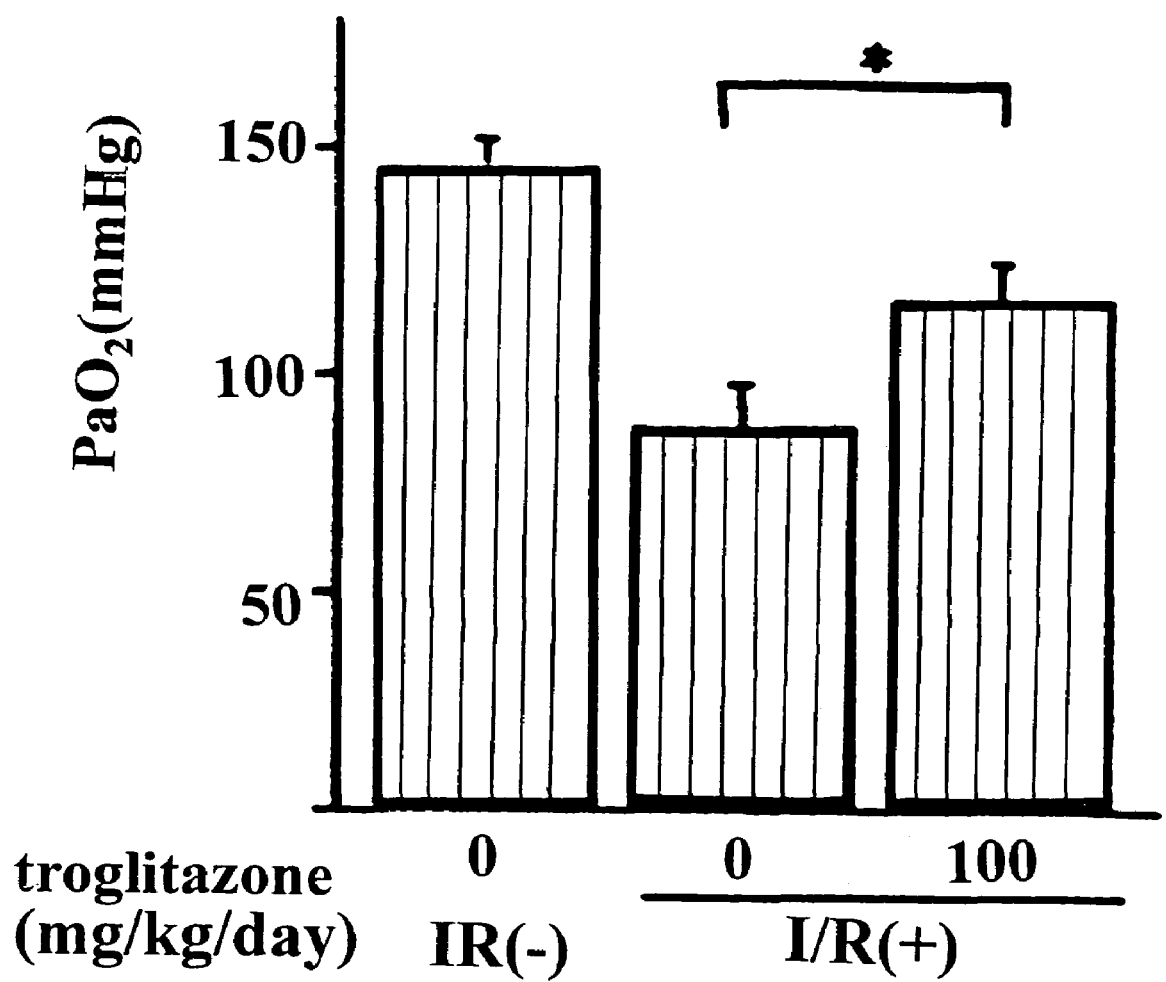
Figure 4B:
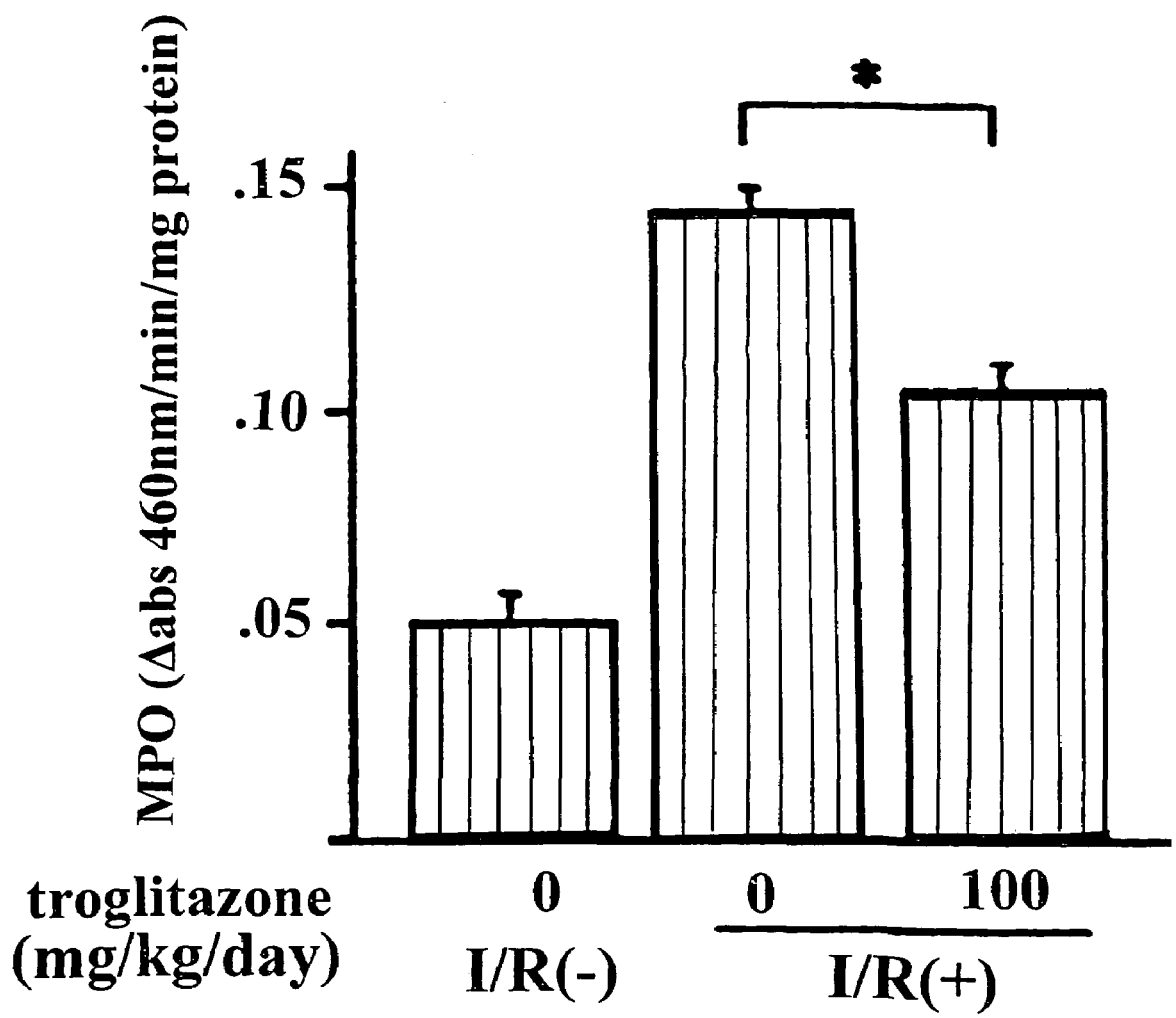

To ascertain the functional effects of PPAR-γ activation in ischemia/reperfusion-injured lungs, measurement of gas exchange was performed after having treated mice with vehicle alone or with troglitazone. As a critical hallmark of lung injury in the setting of ischemia/reperfusion is impaired gas exchange, arterial oxygenation (PaO$_2$) was measured following circulatory exclusion of the nonischemic (right) lung. Arterial oxygenation remained excellent following circulatory exclusion of the right lung in untreated animals whose left lungs were not subjected to ischemia/reperfusion (leftmost bar FIG. 4a). Although arterial oxygenation markedly deteriorated in mice whose left lungs were subjected to ischemia/reperfusion in the absence of troglitazone pretreatment, arterial oxygenation was significantly increased in mice pretreated with troglitazone. To investigate whether inflammatory tissue injury was also affected by PPAR-γ activation, myeloperoxidase activity in lungs was measured as an index of leukocyte accumulation. Troglitazone significantly reduced the elevated levels of myeloperoxidase activity observed after ischemia/reperfusion (FIG. 4b).

Effects of Troglitazone on Cytokine/Chemokine Expression

Figure 4C:
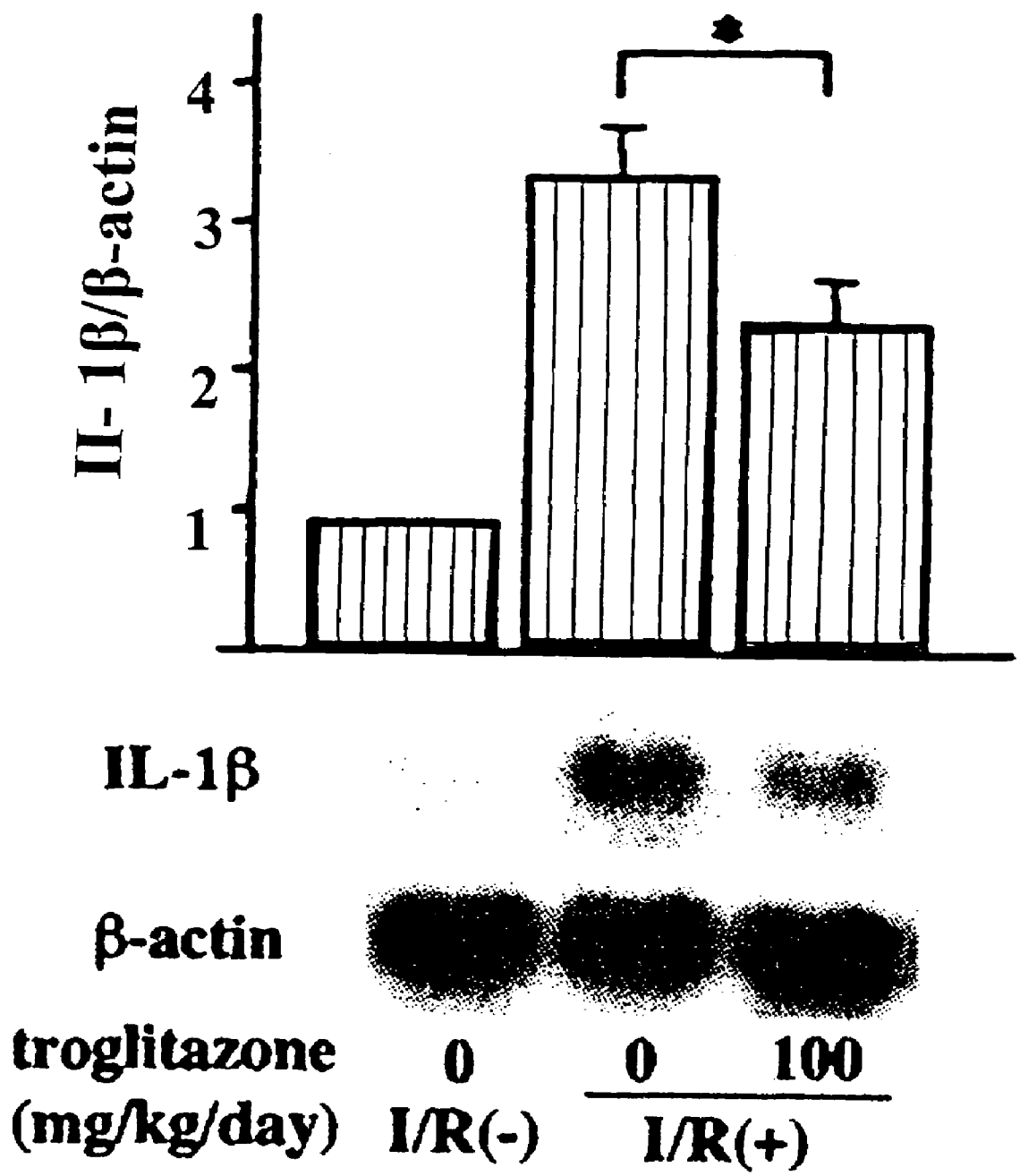
Figure 4D:
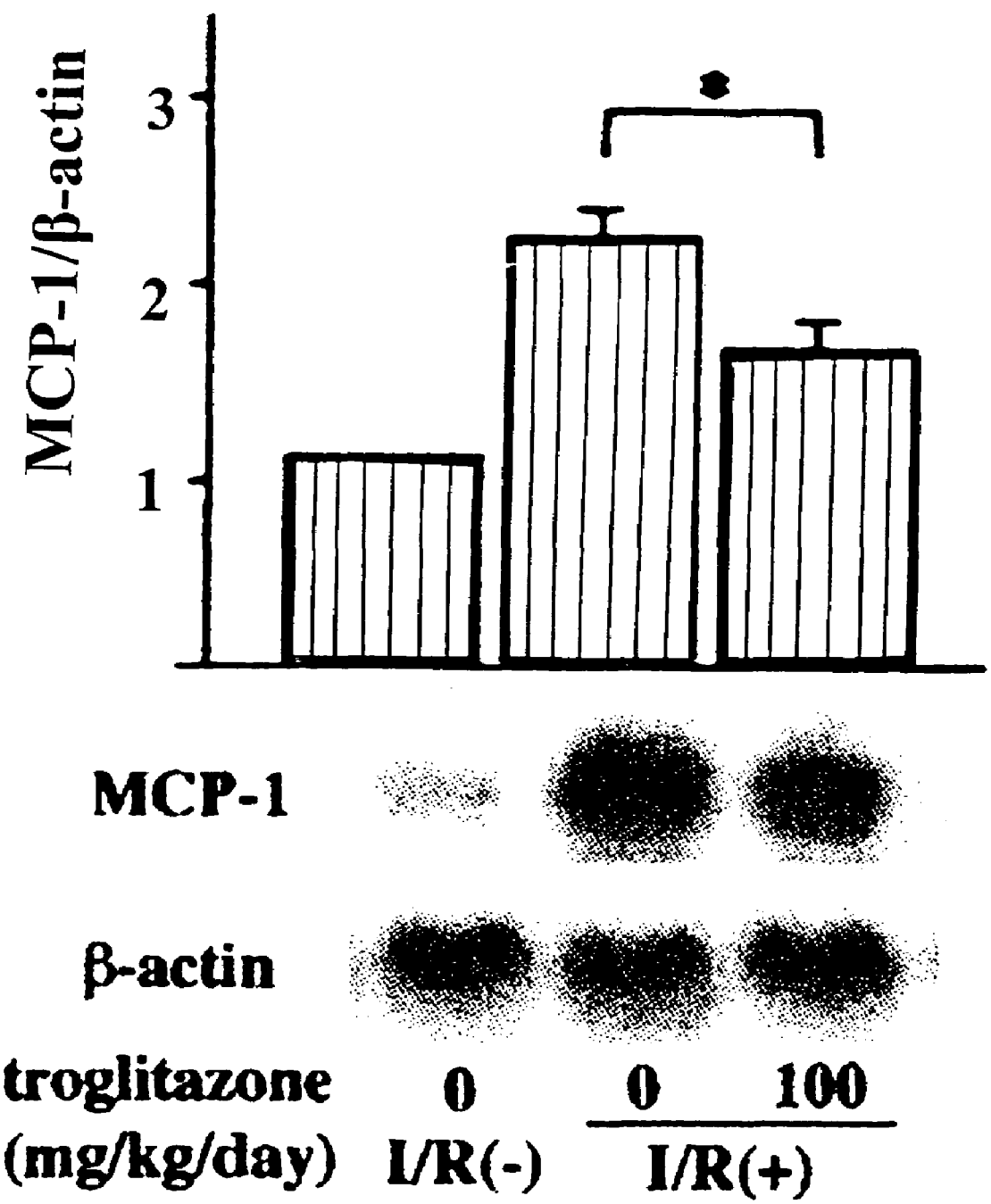
Figure 4E:
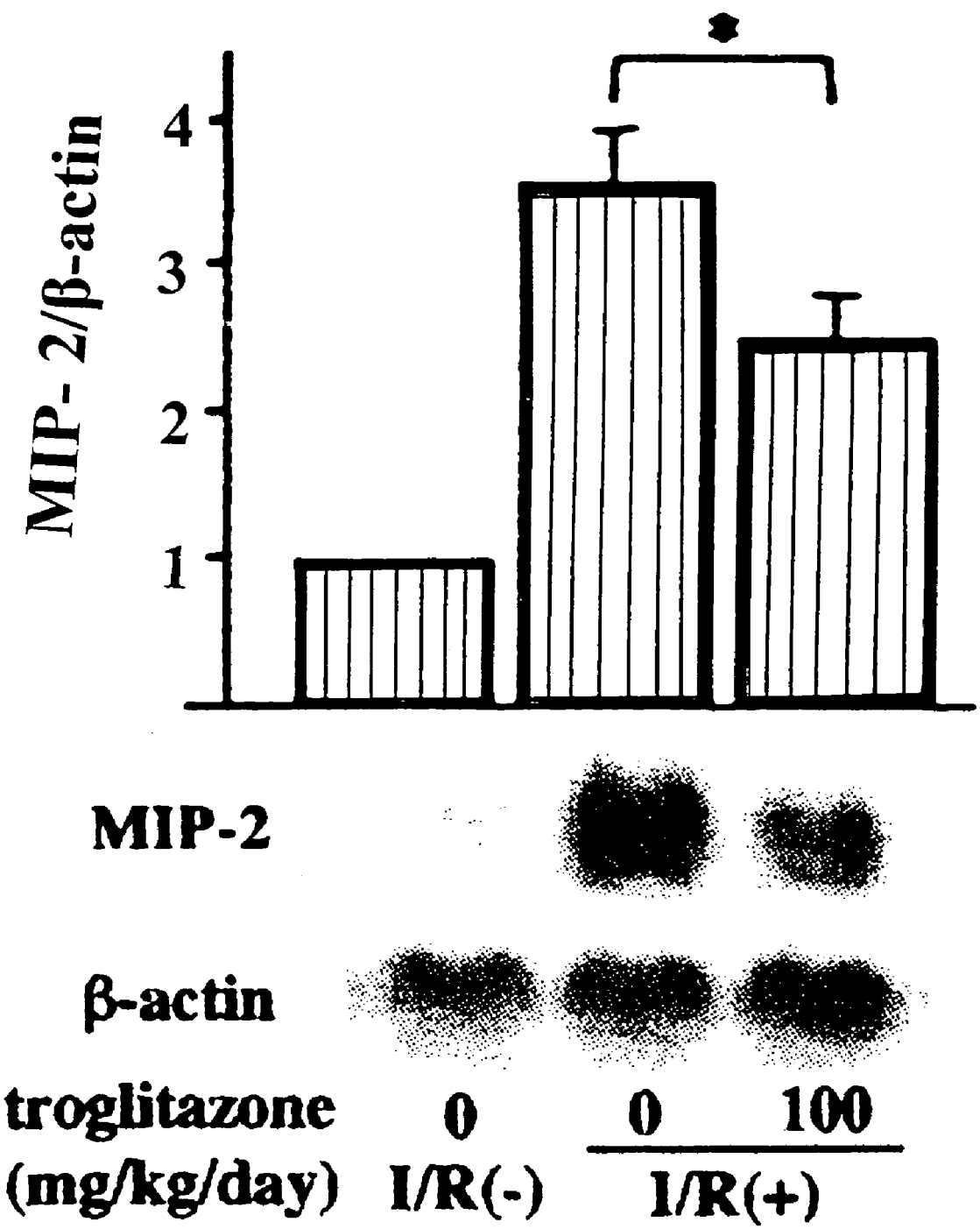

A major facet of the clinical response to tissue ischemia/reperfusion injury results from amplification of the inflammatory response. To investigate the contribution of proinflammatory cytokines to postischemia/reperfusion lung injury, the expression of several prototypical Egr-1 inflammatory target genes was examined. IL-1β mRNA expression was strongly upregulated in lungs exposed to ischemia/ reperfusion; this upregulation was significantly suppressed by administration of troglitazone, but not vehicle (FIG. 4c). Because of the prominent role for recruited leukocytes in lung ischemia/reperfusion injury, expression of the Egr-1 target genes MCP-1 and MIP-2 were examined. MCP-1 and MIP-2 are CC and CXC chemokines which predominantly direct monocytes and neutrophils (respectively) to sites of inflammation (Furie, 1995; and Miura, 2001). Lungs subjected to ischemia/reperfusion showed elevated mRNA levels of MCP-1 and MIP-2 transcripts (FIGS. 4d and 4e), but these increases were significantly suppressed by the PPAR-γ agonist troglitazone.

Figure 4F:
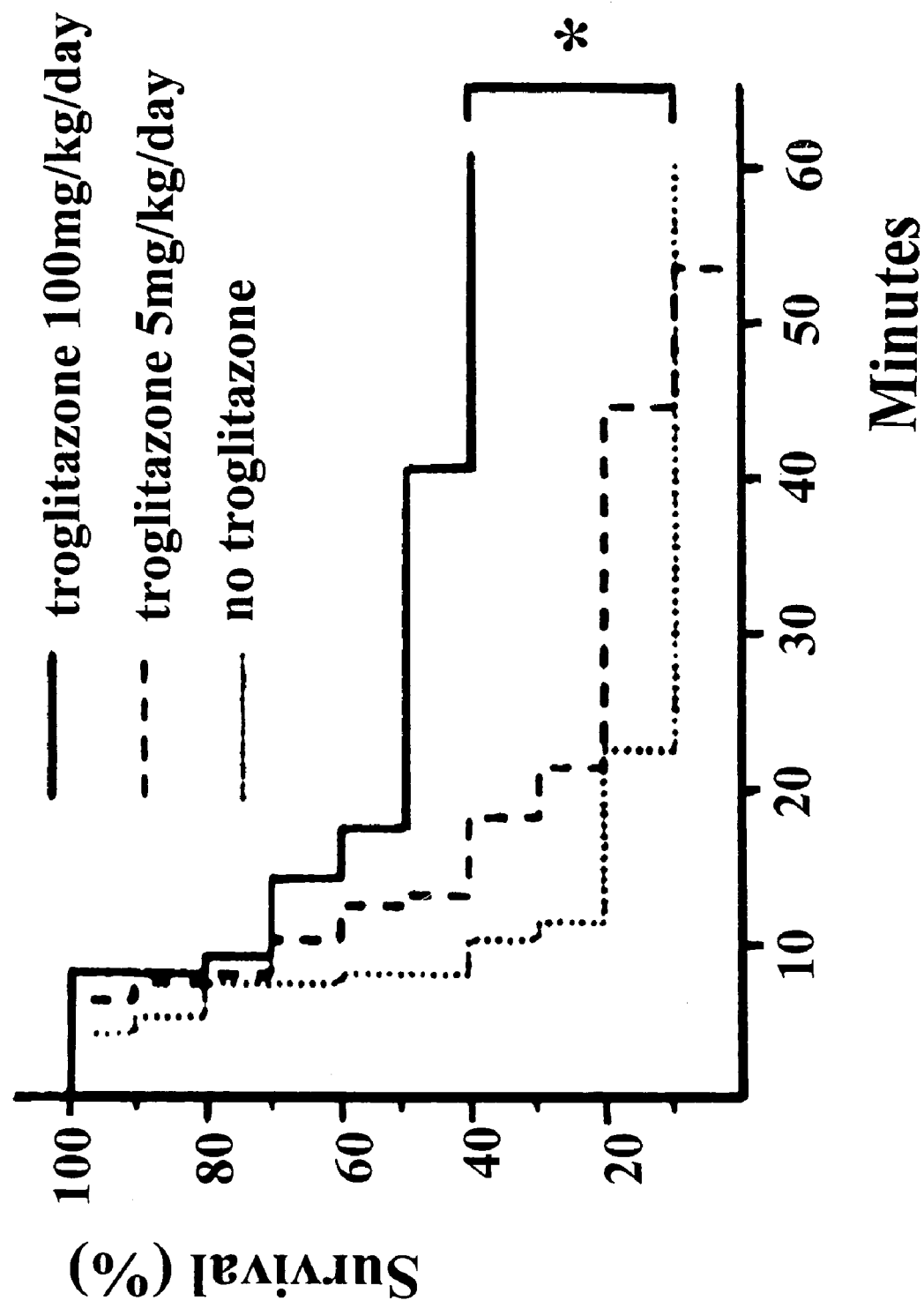

Effects of Troglitazone on Murine Survival Following Lung Ischemia/Reperfusion Injury Survival of mice exposed to ischemia/reperfusion depends on the convergence of a multitude of competing effector mechanisms. Therefore, the effect of troglitazone on murine survival was tested in a stringent model, in essence to summate all effector mechanisms which may be actuated or suppressed in vivo. Although survival was extremely poor following following ischemia of 1 hour and reperfusion of 3 hours at the predefined endpoint of 1 hour after circulatory exclusion of the nonischemic lung in vehicle-treated mice (10% survival), troglitazone-treated mice fared 4 times better (40% survival, FIG. 4f). These data demonstrate that pretreatment with the PPAR-γ agonist troglitazone, which not only suppresses Egr-1 gene expression but also reduces expression of Egr-1 target genes, confers both functional and survival advantages in the setting of lung ischemia/reperfusion injury.

D. Discussion

Lack of oxygen at a systemic or a cellular level comprises a critical component of the ischemic vascular milieu, and has been shown to trigger the rapid induction of Egr-1 both in vitro and in vivo (Yan, 2000; and Yan, 1999). The consequence of this activation is the induced expression of the protein products of divergent families of genes, which are teleologically related in that they all modulate the tissue response to injury. Egr-1 mRNA, protein and activity are barely detectable under baseline conditions, but there is a rapid and pronounced expression of each following lung ischemia/reperfusion or hypoxia in murine models (Yan, 2000). Because many different genes possess Egr-1 response elements in their promoter regions, there are many different gene families whose induction is triggered by ischemic stress through the activation of Egr-1. These include procoagulant genes such as tissue factor and plasminogen activator inhibitor-1, as well as inflammatory genes such as intercellular adhesion molecule-1, IL-1β and chemokines (Yan, 2000). Cytokine expression goes up markedly following bouts of ischemia and reperfusion (Herskowitz, 1995; and Heemann, 2000), and this cytokine expression is causally related to deleterious clinical consequences. Recent work demonstrates that in a lung transplant model, a strategy of Egr-1 suppression can prevent ischemia/reperfusion-induced inflammation and protect the vulnerable lungs by dampening the production of cytotoxic and proinflammatory cytokines (Okada, 2001). However, it should be emphasized that the antisense Egr-1 oligodeoxynucleotide approach used in the lung transplant model is not likely to be applicable to a number of clinical settings in which similar Egr-1 triggered mechanisms of tissue injury apply. Therefore, the instant invention is important in that it links two endogenous transcriptional pathways (PPAR-γ and Egr-1) which interact in ischemic tissue to modulate expression of genes responsible for tissue injury. PPAR-γ agonists are currently in widespread clinical use for insulin sensitization in diabetics. The instant invention demonstrates an important endogenous pathway which is modulated by PPAR-γ agonists, for which there are currently no approved therapeutic modalities.

Treatment with troglitazone significantly inhibits ischemia-driven activation of Egr-1 both in vitro and in vivo, illustrating a new transcriptional mechanism by which PPAR-γ agonists may protect against inflammation. Stimulating the PPAR-γ pathway resulted in a significant improvement in lung function and survival, a decrease in mRNA levels of IL-1β, MIP-2 and MCP-1 expression, as well as a reduction in leukostasis in murine model of lung ischemia/ reperfusion-induced injury. Because these genes are downstream targets of Egr-1 (Yan, 2000), this suggests a functional link between PPAR-γ-mediated inhibition of Egr-1 activation in ischemic lung tissue and improved lung function and survival. Because chemokine-mediated leukocyte recruitment has a pivotal role in controlling the inflammatory reaction to ischemic injury (Adams, 1997), the reduction of which is recognized to enhance postischemic organ function, these data suggest a potential cascade by which PPAR-γ activation can lead to protection against ischemia/ reperfusion-related injury.

Activation of PPAR-γ inhibits vascular cell adhesion molecule expression in endothelial cells, leading to inflammatory actions of macrophages implicated in vascular injury (Jiang, 1998). Endogenous PPAR-γ also protects against intestinal ischemia/reperfusion injury (Nakajima, 2001), with a suggested mechanism requiring suppression of the transcription factor NF-κB. A role for PPAR-γ as a negative modulator of the expression of proinflammatory genes through antagonism of the activities of other transcription factors such as activator protein-1, and signal transducers and activators of transcription-1 has been suggested (Ricote, 1998; Ricote, 1999; and Schoonjans, 1997). The current data are the first to implicate a link between PPAR-γ and Egr-1 in the setting of ischemia/reperfusion injury.

The current studies do not completely exclude the possibility that troglitazone inhibits Egr-1 expression through additional mechanisms which are independent of PPAR-γ. Troglitazone has a vitamin E moiety that could theoretically contribute to its anti-inflammatory activity through antioxidant effects (Venditti, 2000). Whether the dose of vitamin E provided by troglitazone in the present study is enough to impact vascular injury is doubtful. At 100 mg/kg troglitazone per day, mice received the equivalent of 2 IU of vitamin E, a dose much lower than that reported to affect ischemia/ reperfusion-driven injury (Venditti, 2000; and Venditti, 1999). Furthermore, additional data demonstrates that another PPAR-γ ligand, ciglitazone, which does not contain the vitamin E moiety, also suppresses hypoxia-driven Egr-1 induction in macrophages (data not shown). Additional evidence supporting the assumption that the suppressive effect of troglitazone on Egr-1 expression was not dependent on antioxidant effects is provided by a parallel study showing that the natural ligand, 15-d-$PGJ_2$, which has among its properties a direct binding affinity with PPAR-γ inhibited hypoxia-induced expression of Egr-1 in macrophages with equal potency as troglitazone (data not shown).

These data support the existence of a biologically relevant link between two pathways of transcriptional activation, PPAR-γ and Egr-1, in the setting of ischemia and reperfusion injury. Given the potential for harm mediated by Egr-1 induction in hypoxic or ischemic tissue, these data open the door to a new therapeutic modality for Egr-1 suppression and tissue protection relevant for disease such as myocardial infarction and stroke and conditions such as organ transplantation.

REFERENCES

1. Adams, D. H., and Lloyd, A. R. (1997) Chemokines: leucocyte recruitment and activation cytokines. Lancet 349:490–495.
2. Brun, R. P., Tontonoz, P., Forman, B. M., Ellis, R., Chen, J., Evans, R. M., and Spiegelman, B. M. (1996) Differential activation of adipogenesis by multiple PPAR isoforms. Genes. Dev. 10:974–984.
3. Dignam, J. D., Lebovitz, R. M., and Roeder, R. G. (1983) Accurate transcription initiation by RNA polymerase II in a soluble extract from isolated mammalian nuclei. Nucleic. Acids. Res. 11:1475–1489.
4. Forman, B. M., Tontonoz, P., Chen, J., Brun, R. P., Spiegelman, B. M., and Evans, R. M. (1995) 15-Deoxy-delta 12, 14-prostaglandin J2 is a ligand for the adipocyte determination factor PPAR gamma. Cell 83:803–812.
5. Furie, M. B., and Randolph, G. J. (1995) Chemokines and tissue injury. Am. J. Pathol. 146:1287–1301.
6. Gashler, A., and Sukhatme, V. P. (1995) Early growth response protein 1 (Egr-1): prototype of a zinc-finger family of transcription factors. Prog. Nucleic. Acid. Res. Mol. Biol. 50:191–224.
7. Goldblum, S. E., Wu, K. M., and Jay, M. (1985) Lung myeloperoxidase as a measure of pulmonary leukostasis in rabbits. J. Appl. Physiol. 59:1978–1985.
8. Heemann, U., Szabo, A., Hamar, P., Muller, V., Witzke, O., Lutz, J., and Philipp, T. (2000) Lipopolysaccharide pretreatment protects from renal ischemia/reperfusion injury: possible connection to an interleukin-6-dependent pathway. Am. J. Pathol. 156:287–293.
9. Herskowitz, A., Choi, S., Ansari, A. A., and Wesselingh, S. (1995) Cytokine mRNA expression in postischemic/reperfused myocardium. Am. J. Pathol. 146:419–428.
10. Jiang, C., Ting, A. T., and Seed, B. (1998) PPAR-gamma agonists inhibit production of monocyte inflammatory cytokines. Nature 391:82–6.
11. Lehmann, J. M., Moore, L. B., Smith-Oliver, T. A., Wilkison, W. O., Willson, T. M., and Kliewer, S. A. (1995) An antidiabetic thiazolidinedione is a high affinity ligand for peroxisome proliferator-activated receptor gamma (PPAR gamma). J. Biol. Chem. 270:12953–12956.
12. Milbrandt, J. (1987) A nerve growth factor-induced gene encodes a possible transcriptional regulatory factor. Science 238:797–799.
13. Miura, M., Fu, X., Zhang, Q. W., Remick, D. G., and Fairchild, R. L. (2001) Neutralization of Gro alpha and macrophage inflammatory protein-2 attenuates renal ischemia/reperfusion injury. Am. J. Pathol. 159:2137–2145.
14. Nakajima, A., Wada, K., Miki, H., Kubota, N., Nakajima, N., Terauchi, Y., Ohnishi, S., Saubermann, L. J., Kadowaki, T., Blumberg, R. S., Nagai, R., and Matsuhashi, N. (2001) Endogenous PPAR gamma mediates anti-inflammatory activity in murine ischemia-reperfusion injury. Gastroenterology 120:460–469.
15. Nguyen, H. Q., Hoffman-Liebermann, B., and Liebermann, D. A. (1993) The zinc finger transcription factor Egr-1 is essential for and restricts differentiation along the macrophage lineage. Cell 72:197–209.
16. Okada, M., Fujita, T., Sakaguchi, T., Olson, K. E., Collins, T., Stern, D. M., Yan, S. F., and Pinsky, D. J. (2001) Extinguishing Egr-1-dependent inflammatory and thrombotic cascades after lung transplantation. FASEB. J. 15:2757–2759.
17. Ricote, M. F., Li, A. C., Willson, T. M., Kelly, C. J., and Glass, C. K. (1998) The peroxisome proliferator-activated receptor-gamma is a negative regulator of macrophage activation. Nature 391:79–82.
18. Ricote, M., Huang, J. T., Welch, J. S., and Glass, C. K. (1999) The peroxisome proliferator-activated receptor (PPAR-gamma) as a regulator of monocyte/macrophage function. J. Leukoc. Biol. 66:733–739.
19. Schoonjans, K., Martin, G., Staels, B., Auwerx, J. (1997) Peroxisome proliferator-activated receptors, orphans with ligands and functions. Curr. Opin. Lipidol. 8:159–166.
20. Tontonoz, P., Hu, E., and Spiegelman, B. M. (1994) Stimulation of adipogenesis in fibroblasts by PPAR gamma 2, a lipid-activated transcription factor. Cell 79:1147–156.
21. Venditti, P., Masullo, P., Di Meo, S., and Agnisola, C. (1999) Protection against ischemia-reperfusion induced oxidative stress by vitamin E treatment. Arch. Physiol. Biochem. 107:27–34.
22. Venditti, P., Masullo, P., Agnisola, C., and Di Meo, S. (2000) Effect of vitamin E on the response to ischemia-reperfusion of Langendorff heart preparations from hyperthyroid rats. Life Sci. 66:697–708.
23. Yan, S. F., Tritto, I., Pinsky, D., Liao, H., Huang, J., Fuller, G. F., Brett, J., May, L., and Stern, D. (1995) Induction of interleukin 0.6 (IL-6) by hypoxia in vascular cells. Central role of the binding site for nuclear factor-IL-6. J. Biol. Chem. 270:11463–11471.
24. Yan, S. F., Lu, J., Zou, Y. S., Soh-Won, J., Cohen, D. M., Buttrick, P. M., Cooper, D. R., Steinberg, S. F., Mackman, N., Pinsky, D. J., and Stern, D. M. (1999) Hypoxia-associated induction of early growth response-1 gene expression. J. Biol. Chem. 274:15030–15040.
25. Yan, S. F., Fujita, T., Lu, J., Okada, K., Shan Zou, Y., Mackman, N., Pinsky, D. J., and Stern, D. M. (2000) Egr-1, a master switch coordinating upregulation of divergent gene families underlying ischemic stress. Nature Medicine 6:1355–1361.

What is claimed is:

1. A method for determining whether an agent increases PPAR-γ-mediated inhibition of Egr-1 expression in a cell comprising
    (a) (i) contacting the agent with the cell, and (ii) subjecting the cell to a stimulus known to increase Egr-1 expression in a cell, wherein steps (i) and (ii) are performed concurrently or in sequence;
    (b) determining the amount of Egr-1 expression in the cell;
    (c) comparing the amount of Egr-1 expression determined in step (b) to the amount of Egr-1 expression observed in the cell in the absence of the agent, wherein the amount of Egr-1 expression in the absence of the agent being greater than that in the presence of the agent indicates that the agent inhibits Egr-1 expression in the cell; and
    (d) comparing the amount of Egr-1 expression determined in step (b) with the amount of Egr-1 expression observed in the presence of the agent and under conditions known to inhibit PPAR-γ activation, wherein the amount of Egr-1 expression in the presence of the agent under such conditions being greater than that determined in step (b) indicates that the agent increases PPAR-γ-mediated inhibition of Egr-1 expression.

2. The method of claim 1, wherein the cell is a human cell.

3. The method of claim 1, wherein the cell is a mononuclear phagocyte, a lymphocyte, a neutrophil, an endothelial cell, an epithelial cell, a smooth muscle cell, a neuron or a hepatocyte.

4. The method of claim 1, wherein the stimulus is hypoxia or administration of an inflammatory agent.

5. The method of claim 1, wherein determining the amount of Egr-1 expression comprises determining the amount of Egr-1 protein present in the cell.

6. The method of claim 1, wherein determining the amount of Egr-1 expression comprises determining the amount of Egr-1 mRNA present in the cell.

7. The method of claim 1, wherein determining the amount of Egr-1 expression comprises determining the amount of Egr-1 protein present in the cell which binds to a nucleic acid comprising an Egr-1 binding site.

8. The method of claim 1, wherein the conditions known to inhibit PPAR-γ activation comprise contact with a PPAR-γ antagonist or an anti-PPAR-γ antibody.

9. The method of claim 1, wherein the cell is a mononuclear phagocyte, the stimulus is hypoxia, and determining the amount of Egr-1 expression in the cell is performed by determining the amount of Egr-1 mRNA present in the cell.

* * * * *